(12) United States Patent
Abbott et al.

(10) Patent No.: US 7,531,366 B2
(45) Date of Patent: May 12, 2009

(54) BEAD BASED ASSAYS USING A LIQUID CRYSTAL REPORTER

(75) Inventors: Nicholas Abbott, Madison, WI (US);
Christopher Murphy, Madison, WI (US); Barbara Israel, Mt Horeb, WI (US); Doug Hansmann, Madison, WI (US)

(73) Assignee: Platypus Technologies, LLC, Madison, WI (US)

( * ) Notice: Subject to any disclaimer, the term of this patent is extended or adjusted under 35 U.S.C. 154(b) by 298 days.

(21) Appl. No.: 11/328,040

(22) Filed: Jan. 9, 2006

(65) Prior Publication Data

US 2006/0252031 A1    Nov. 9, 2006

Related U.S. Application Data

(63) Continuation-in-part of application No. 10/897,626, filed on Jul. 23, 2004.

(60) Provisional application No. 60/642,237, filed on Jan. 7, 2005.

(51) Int. Cl.
*G01N 33/553* (2006.01)
*C12Q 1/70* (2006.01)
*G01N 33/53* (2006.01)
*G02F 1/13* (2006.01)
*C09K 19/02* (2006.01)
*C12M 1/34* (2006.01)

(52) U.S. Cl. .............................. 436/526; 435/5; 435/7.1; 435/287.2; 435/287.3; 435/288.7; 349/1; 349/182; 349/183; 422/55

(58) Field of Classification Search .................. None
See application file for complete search history.

(56) References Cited

U.S. PATENT DOCUMENTS

| | | | |
|---|---|---|---|
| 6,171,802 B1 | 1/2001 | Woolverton |
| 6,284,197 B1 | 9/2001 | Abbott |
| 6,288,392 B1 | 9/2001 | Abbott |
| 6,692,699 B2 | 2/2004 | Abbott |
| 6,780,492 B2 | 8/2004 | Hawker et al. |
| 6,797,463 B2 | 9/2004 | Abbott |
| 6,824,837 B2 | 11/2004 | Abbott |
| 6,849,321 B2 | 2/2005 | Abbott |
| 6,852,285 B2 | 2/2005 | Abbott |

(Continued)

FOREIGN PATENT DOCUMENTS

WO          9963329           12/1999

(Continued)

OTHER PUBLICATIONS

Gupta, et al. Optical Amplification of Ligand-Receptor Binding Using Liquid Crystals. Science. 1998; 279;2077-2080.*

(Continued)

*Primary Examiner*—Mary E Mosher
*Assistant Examiner*—Stuart W Snyder
(74) *Attorney, Agent, or Firm*—Casimir Jones, S.C.

(57) ABSTRACT

The present invention relates to the field of detection of analytes, and in particular to detection of viruses, cells, bacteria, lipid-membrane containing organisms, proteins, nucleic acids, carbohydrates and other biomolecules, organic molecules and inorganic molecules using a liquid crystal assay format.

15 Claims, 13 Drawing Sheets

Elution buffer    BSA 200ng/mL    F1 5ng/mL    F1 10ng/mL    F1 50ng/mL    F1 200ng/mL

U.S. PATENT DOCUMENTS

| | | |
|---|---|---|
| 6,858,423 B1 | 2/2005 | Abbott |
| 7,018,838 B2 | 3/2006 | Murphy |
| 7,125,592 B2 | 10/2006 | Abbott |
| 7,135,143 B2 | 11/2006 | Abbott |
| 7,303,694 B2 | 12/2007 | Abbott |
| 2002/0004216 A1 | 1/2002 | Abbott |
| 2002/0028451 A1 | 3/2002 | Abbott |
| 2002/0055093 A1 | 5/2002 | Abbott |
| 2002/0142453 A1 | 10/2002 | Abbott |
| 2002/0164604 A1 | 11/2002 | Abbott |
| 2003/0071949 A1 | 4/2003 | Abbott |
| 2003/0099993 A1 | 5/2003 | Abbott |
| 2003/0127396 A1* | 7/2003 | Siddiqi .................. 210/695 |
| 2003/0180966 A1 | 9/2003 | Abbott |
| 2003/0194753 A1 | 10/2003 | Abbott |
| 2004/0038408 A1 | 2/2004 | Abbott |
| 2004/0091620 A1 | 5/2004 | Abbott |
| 2004/0161800 A1 | 8/2004 | Abbott |
| 2005/0064395 A1 | 3/2005 | Abbott |
| 2005/0079486 A1 | 4/2005 | Abbott |
| 2005/0079487 A1 | 4/2005 | Abbott |
| 2005/0106562 A1 | 5/2005 | Abbott |
| 2005/0221271 A1 | 10/2005 | Abbott |
| 2005/0260703 A1 | 11/2005 | Abbott |
| 2006/0003389 A1 | 1/2006 | Abbott |
| 2006/0141446 A1 | 6/2006 | Abbott |
| 2006/0252031 A1 | 11/2006 | Abbott |
| 2007/0004046 A1 | 1/2007 | Abbott |
| 2007/0042505 A1 | 2/2007 | Abbott |
| 2007/0099249 A1 | 5/2007 | Abbott |
| 2007/0104612 A1 | 5/2007 | Abbott |
| 2007/0110614 A1 | 5/2007 | Abbott |
| 2007/0231832 A1 | 10/2007 | Abbott |
| 2007/0269848 A1 | 11/2007 | Abbott |
| 2008/0050799 A1 | 2/2008 | Abbott |
| 2008/0160539 A1 | 7/2008 | Abbott |

FOREIGN PATENT DOCUMENTS

| | | |
|---|---|---|
| WO | 0161325 | 8/2001 |
| WO | 0161357 | 8/2001 |
| WO | 02/071929 A2 | 9/2002 |
| WO | WO02071929 A2 * | 9/2002 |

OTHER PUBLICATIONS

Tingey, et al. Imaging of Affinity Microcontact Printed Proteins by Using Liquid Crystals. Langmuir 2004, 20, 6818-6826.*

Espinoza LA, Schumann KR, Luk YY, Israel BA, Abbott NL; Orientational Behavior of Thermotropic Liquid Crystals On Surfaces Presenting Electrostatically Bound Vesicular Stomatitis Virus. Langmuir (Mar. 16, 2004); 20(6):2375-85.

Seung-Ryeol Kim, Rahul R. Shah

Elution buffer    BSA 200ng/mL    F1 5ng/mL    F1 10ng/mL    F1 50ng/mL    F1 200ng/mL BSA      F1 200ng      F1 40ng      F1 8ng

BEAD BASED ASSAYS USING A LIQUID CRYSTAL REPORTER

This application is a continuation-in-part of U.S. application Ser. No. 10/897,626, filed Jul. 23, 2004 and claims the benefit of U.S. Prov. Appl. Ser. No. 60/642,237 filed Jan. 7, 2005, each of which is incorporated herein by reference.

This invention was made with government support under Grant No. 5R43AI4960602 awarded by the National Institute of Allergy and Infectious Disease and Grant No. 1R43CA117215-01 awarded by the National Cancer Institute. The Government has certain rights in the invention.

FIELD OF THE INVENTION

The present invention relates to the field of detection of analytes, and in particular to detection of viruses, cells, bacteria, lipid-membrane containing organisms, proteins, nucleic acids, carbohydrates and other biomolecules, organic molecules and inorganic molecules using a liquid crystal assay format.

BACKGROUND OF THE INVENTION

The detection of pathogen, protein, and nucleic acid targets in biological samples forms the basis of the multi-billion dollar in vitro diagnostic industry. Detection of protein and nucleic acid targets can be divided into diagnostic and research based markets. The diagnostic market includes the detection and identification of pathogens such as viruses and bacteria, the identification of various genetic markers, and the identification of markers associated with the presence of tumors. The research market includes the genomics and proteomics industries, which require analytical, drug discovery, and high-throughput screening technologies.

Initial viral diagnostics consisted of the crude, albeit sensitive and non-specific techniques of direct inoculation of sample material into suckling mice, embryonated eggs, or living cells. Diagnostic methods have since evolved to the sensitive, specific, but time consuming serological techniques of neutralization, ELISA and fluorescent antibody assays and subsequently to the current highly sensitive, instrumentation-dependent techniques of nucleic acid amplification and luminescent bead-based assays. This evolution in approach to virus detection and identification has been driven by advances in biology (cell culture, immunology), followed by advances in biochemistry (immunochemistry, molecular biology, dye chemistry). More recent progress comes from advances in instrumentation sciences (optics, electronics, robotics, miniaturization, microfluidics, etc.) and by the subsequent interfacing of microelectronics with biology to develop the first generation of biosensors.

There are many ways to detect the presence of a virus in a sample. Methods with the highest sensitivity (real-time PCR, tissue culture, electron microcopy) also involve the highest complexity and/or cost, require sophisticated equipment and facilities and require highly trained personnel. Methods with less sensitivity (IFA, ELISA, dipstick methods), in practice, suffer from cross-reactivity problems, involve more hands-on time and/or are less adaptable to rapidly screening large numbers of samples. There is a great need for multiplexing in situations such as arbovirus surveillance, bio-threat monitoring, and for rapid agent identification during a disease outbreak of unknown origin. In practice, nucleic acid techniques and bead-based techniques currently can multiplex approximately 6-20 different targets.

Though there are many techniques available to detect and identify viruses, there is need for improvement. Among the desired attributes are: lower cost, less reliance on biological systems, less reliance on use of labile, expensive reagents, less complexity in execution, decreased hands-on time required for processing the sample and execution of the assay, minimal technical proficiency for running assays and interpreting results, miniaturization and portability of equipment, automation, and an increase in multiplexing capability.

SUMMARY OF THE INVENTION

The present invention relates to the field of detection of analytes, and in particular to detection of viruses, cells, bacteria, lipid-membrane containing organisms, proteins, nucleic acids, carbohydrates and other biomolecules, organic molecules and inorganic molecules using a liquid crystal assay format.

Accordingly, in some embodiments, the present invention provides a system comprising: magnetic beads functionalized with a recognition moiety; and a substrate that orients liquids crystals. In some embodiments, the system further comprises a magnet (e.g., a permanent magnet or an electric magnet). In certain embodiments, the system further comprises a tube and a pump, wherein the pump is fluidically connected to the tube and the tube is positioned to be exposed to the magnetic field of the magnet. In some embodiments, the tube has an inner surface with a diameter so that the surface tension energy of a fluid within the tube is larger than the surface energy of the tube so that a pressure gradient between the two ends of the tube induces movement of the fluid plugs inside the tube without wetting the inner surface. In some embodiments, the tube is movable with respect to the magnet. In other embodiments, the tube is rotatable. In some embodiments, the magnetic beads are located in the tube so as to be attractable by the magnet. The present invention is not limited to a particular substrate. A variety of substrates are contemplated for use in the present invention including, but not limited to, a polyimide coated substrate, an anisotropic gold substrate, or a rubbed substrate. In some embodiments, the substrate comprises microfluidic channels that orient liquid crystals. In certain embodiments, the substrate comprises PDMS. In some embodiments, the tube is made from glass or plastic. In some embodiments, the system further comprises a stamp. In other embodiments, the system further comprises mesogens (e.g., 4-cyano-4'-pentylbiphenyl, N-(4methoxybenzylidene)-4-butlyaniline or combinations thereof). In some embodiments, the recognition moiety is a protein, peptide, polypeptide, nucleic acid, carbohydrate or organic compound. In some embodiments, the Analyte is a protein, peptide, polypeptide, nucleic acid, carbohydrate or an organic compound.

The present invention further provides a method comprising providing magnetic beads functionalized with a recognition moiety that binds an analyte; a substrate that orients liquid crystals; a sample suspected of containing an analyte; a magnet; and mesogens; contacting the magnetic beads with the sample under conditions such that the analate binds to the recognition moiety; attracting the beads with the magnet; washing the magnetic beads; eluting the analyte from the beads onto to the substrate; and contacting the substrate with the mesogens under conditions such that the presence of the Analyte on the substrate can be detected.

The present invention also provides a kit comprising magnetic beads functionalized with a recognition moiety; and a substrate that orients liquids crystals.

The present invention additionally provides a method comprising providing: a tube comprising magnetic beads functionalized with a recognition moiety that binds an analyte; a magnet (e.g., a permanent magnet or an electric magnet), and a pump (e.g., a manual pump or an automated pump) fluidically connected to the tube and at least one reservoir comprising an elution solution and at least one reservoir containing a solution suspected of containing an analyte; via the pump, drawing an aliquot of the solution suspected of containing an analyte into the tube; via the pump, drawing an aliquot of the treatment solution into the tube so that the aliquot of the solution suspected of containing an analyte is separated from the aliquot of the elution solution by a volume of air; via the pump, moving the aliquot of the solution suspected of containing an analyte to contact the magnetic beads so that the analyte can bind to the ligand on the magnetic beads; attracting the magnetic beads with the magnet; via the pump, moving the aliquot of the solution suspected of containing an analyte so that it no longer contacts the magnetic beads and moving the aliquot of elution solution to contact the magnetic beads so that the analyte elutes into the elution solution. In some embodiments, the pump is fluidically connected to at least one other reservoir containing a wash solution. In some embodiments, at least one aliquot of the wash solution is loaded into the tube prior to the aliquot of solution suspected of containing an analyte. In other embodiments, at least one aliquot of the wash solution is loaded into the tube between the aliquot of solution suspected of containing an analyte and the aliquot of the elution solution. In still other embodiments, at least one aliquot of the wash solution is loaded into the tube after the aliquot of the elution solution. In some embodiments, a plurality of reservoirs containing different wash solutions are fluidically connected to the pump so that aliquots of the different wash solutions may be loaded into the tube before, in between and/or after the aliquots of the solution suspected of containing an analyte and aliquot of elution solution. In some embodiments, the method further comprises recovering the elution solution. In certain embodiments, the method further comprises detecting the analyte. The present invention is not limited to a particular detection method. Exemplary detection methods include, but are not limited to, Northern blotting, Southern blotting, Western blotting, ELISA, fluorescent detection and liquid crystal detection (e.g., by applying the elution solution to a substrate that orients liquid crystals and applying a liquid crystal to the substrate, wherein the presence of the analyte is indicated by a difference in the ordering of the liquid crystal). In some embodiments, the liquid crystal assumes a random planar orientation over areas of the substrate having bound analyte. In some embodiments, the substrate is a polyimide coated substrate, an anisotropic gold substrate, or a rubbed substrate. In some embodiments, the substrate comprises microfluidic channels that orient liquid crystals. In certain embodiments, the substrate comprises PDMS. In some embodiments, the analyte is a protein, nucleic acid, virus, bacterium, or carbohydrate. In some embodiments, the recognition moiety is a protein, polypeptide, peptide, antibody, nucleic acid, or carbohydrate. In some embodiments, following contacting the beads with an aliquot of solution, the tube is moved to mix the beads with the solution. In some embodiments, the tube is rotated. In some embodiments, the tube is glass or plastic. In some embodiments, the liquid crystal comprises 5CB.

In other embodiments, the present invention provides a kit comprising: magnetic beads; a tube (e.g., a glass tube or a plastic tube); a magnet (e.g., a permanent magnet or a electric magnet); and mesogens. In preferred embodiments, the magnetic beads are functionalizable. In some embodiments, the magnetic beads are functionalized with a ligand. In some embodiments, the kit further comprises at least one container of wash solution. In other embodiments, the kit further comprises at least one aliquot of elution solution. In certain embodiments, the kit further comprises instructions for using the kit to detect an analyte. In some embodiments, the kit further comprises a substrate that orients liquid crystals (e.g., a polyimide coated substrate, an anisotropic gold substrate, or a rubbed substrate). In other embodiments, the substrate comprises microfluidic channels that orient liquid crystals. In yet other embodiments, the substrate comprises PDMS.

In yet other embodiments, the present invention provides a system for parallel processing of samples suspected of containing an analyte comprising: a plate comprising a plurality of wells (e.g., 16, 24, 96, or 384 wells); a plurality of magnetic beads comprising at least one recognition moiety that binds an analyte, the plurality of magnetic beads positioned in sat least one of the wells; a magnet positionable to attract the magnetic beads; and a substrate that orients a liquid crystal. In some embodiments, different subsets of wells comprise magnetic beads functionalized with different recognition moieties. In some embodiments, the subset of wells comprises one or more wells. In some embodiments, at least one of the wells comprises control magnetic beads. In some embodiments, the magnet is insertable between the wells so that the magnetic beads are drawn to the sides of the wells. In some embodiments, the system further comprises a magnet (e.g., a permanent magnet or an electric magnet). In some embodiments, the substrate that orients liquid crystals is a substrate that anisotropically orients liquid crystals or a substrate that homeotropically orients liquid crystals. In other embodiments, the substrate is nanostructured gold, polyimide, or rubbed substrates. In still other embodiments, the substrate comprises microchannels. In some embodiments, the magnetic beads are about 0.8 microns in diameter. In some embodiments, the analyte is a protein, polypeptide, peptide, or a nucleic acid. In other embodiments, the analyte is a cytokine (e.g., interleukin-1 alpha, interleukin-1 beta, interleukin-2, interleukin-4, interleukin-6, interleukin-7, interleukin-8, interleukin-10, interleukin-12, GM-CSF, interferon-gamma, or TNF-alpha). In some embodiments, the recognition moiety is a peptide, polypeptide, protein (e.g., antigen binding protein), or nucleic acid. In some embodiments, the antigen binding protein binds a cytokine. In some embodiments, the system further comprises a stamp substrate comprising at least one projection insertable into at least one well. In some embodiments, the at least one projection comprises a distal end having a stamp surface. In certain embodiments, the stamp surface comprises PDMS. In some embodiments, the stamp surface comprises a recognition moiety. In some embodiments, the recognition moiety on the magnetic bead binds a class of immunoglobulins and the recognition moiety on the stamp surface is specific for an analyte. In other embodiments, the magnetic beads comprise a plurality of recognition moieties specific for more than one class of immunoglobulins and the recognition moiety on the stamp surface binds an analyte. In some embodiments, the immunoglobulin is IgA, IgG, IgM, IgE, or combinations thereof.

In still further embodiments, the present invention provides a method of detecting an analyte comprising: providing a solution suspected of containing an analyte, a wash solution, and an elution solution; a multiwell plate comprising a plurality of wells (e.g., 16, 24, 96, or 384 well plates); a first plurality of magnetic beads functionalized with a recognition moiety, the first plurality of magnetic beads positioned in at least one of the wells; a substrate that orients a liquid crystal; and a magnet (e.g., a permanent magnet or an electric magnet); placing the solution into the at least one well containing the first plurality of magnetic beads so that the magnetic beads bind the analyte; attracting the magnetic beads with the magnet; washing the magnetic beads to provide washed magnetic beads; attracting the washed magnetic beads with the magnet; contacting the washed magnetic beads with aid elution solution so that the analyte is eluted from the beads into the elution solution; contacting the substrate with the elution solution; and applying a liquid crystal to the substrate, wherein the presence of the analyte is indicated by a difference in orientation in a region of the liquid crystal. In some embodiments, different subsets of wells comprise magnetic beads functionalized with different recognition moieties. In some embodiments, the subset of wells comprises one or more wells. In other embodiments, at least one of the wells comprises control magnetic beads. In some embodiments, the magnet is insertable between the wells so that the magnetic beads are drawn to the sides of the wells. In some embodiments, the substrate homerotropically orients liquid crystals. In some embodiments, the substrate is nanostructured gold, polyimide, or a rubbed substrate. In other embodiments, the substrate comprises microchannels. In some embodiments, the magnetic beads are about 0.8 microns in diameter. In some embodiments, the analyte is a protein, polypeptide, peptide, or nucleic acid. In other embodiments, the analyte is a cytokine (e.g., interleukin-1 alpha, interleukin-1 beta, interleukin-2, interleukin-4, interleukin-6, interleukin-7, interleukin-8, interleukin-10, interleukin-12, GM-CSF, interferon-gamma, or TNF-alpha). In some embodiments, the recognition moiety is a peptide (e.g., antigen binding protein) polypeptide, protein, or nucleic acid. In some embodiments, the antigen binding protein binds a cytokine. In some embodiments, the method further comprises providing a stamp substrate comprising at least one projection insertable into at least one well and transferring the analyte to the substrate via the stamp. In some embodiments, the at least one projection comprises a distal end having a stamp surface. In some embodiments, the stamp surface comprises PDMS. In other embodiments, the stamp surface comprises a recognition moiety.

In still other embodiments, the present invention provides a kit comprising: a multiwell plate comprising a plurality of wells; a first plurality of magnetic beads functionalized with a recognition moiety; a magnet (e.g., a permanent magnet or an electric magnet); a container containing wash solution; a container containing elution solution; and a substrate that orients liquid crystals. In some embodiments, the magnet is positionable between the wells of the multiwell plate so that the magnetic beads are attracted to the sides of the wells. In some embodiments, the kit further comprises at least a second plurality of magnetic beads, the second plurality of magnetic beads comprising a different recognition moiety than the first plurality of magnetic beads. In some embodiments, the kit further comprises a container of mesogens. In certain embodiments, the kit further comprises instructions for the detection of an analyte. In some embodiments, the substrate homeotropically orients liquid crystals. In some embodiments, the substrate is nanostructured gold, polyimide, or a rubbed substrate. In other embodiments, the substrate comprises microchannels. In some embodiments, the magnetic beads are approximately 0.8 microns in diameter. In some embodiments, the recognition moiety is a peptide, polypeptide, protein, or nucleic acid. In some embodiments, the protein is an antigen binding protein. In some embodiments, the antigen binding protein binds a cytokine (e.g., interleukin-1 alpha, interleukin-1 beta, interleukin-2, interleukin-4, interleukin-6, interleukin-7, interleukin-8, interleukin-10, interleukin-12, GM-CSF, interferon-gamma, or TNF-alpha). In some embodiments, the kit further comprises a stamp substrate comprising at least one projection insertable into at least one well. In some embodiments, the at least one projection comprises a distal end having a stamp surface. In other embodiments, thee stamp surface comprises PDMS. In some embodiments, the stamp surface comprises a recognition moiety.

In some further embodiments, the present invention provides a method of identifying immunoglobulins of a specific subclass comprising: providing magnetic beads functionalized with antibodies specific for one or more subclasses of immunoglobulins; a solution suspected of containing an immunoglobulin specific for an antigen; a stamp functionalized with the antigen; a substrate that orients liquid crystals; contacting the magnetic beads with the solution so that the magnetic beads bind at least a first subclass of immunoglobulins but do not bind a second subclass of immunoglobulins; contacting the solution with the stamp so that the second subclass of immunoglobulins binds to the stamp; transferring the second class of immunoglobulins to the substrate; and forming a liquid crystal on the substrate, wherein the presence of the second subclass of immunoglobulins is indicated by a region of difference in the orientation of the liquid crystal. In some embodiments, the at least first subclass of immunoglobulins comprises IgG and the second subclass of immunoglobulins comprises IgM.

In yet other embodiments, the present invention provides a kit for detecting immunoglobulins of a specific subclass comprising: magnetic beads functionalized with antibodies specific for one or more subclasses of immunoglobulins; a stamp functionalized with an antigen; and a substrate that orients liquid crystals. In some embodiments, the magnetic beads are functionalized with antibodies that bind IgG. In other embodiments, the magnetic beads are functionalized with antibodies that bind IgG and IgM. In some embodiments, the substrate homeotropically orients liquid crystals. In some embodiments, the kit further comprises a multiwell plate. In some embodiments, the kit further comprises a container of mesogens.

DEFINITIONS

Figure 1:
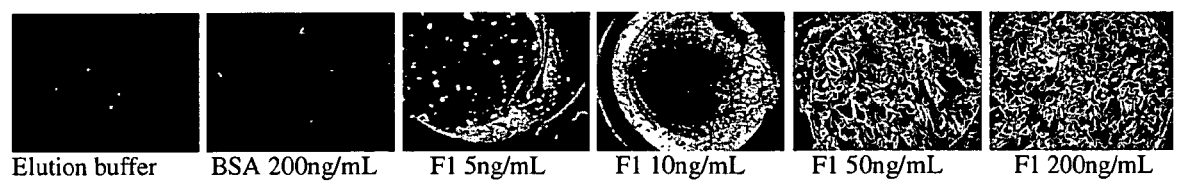
FIG. 1 is an image of an assay using a polyimide coated substrate to non-specifically detect an analyte.
Figure 2:
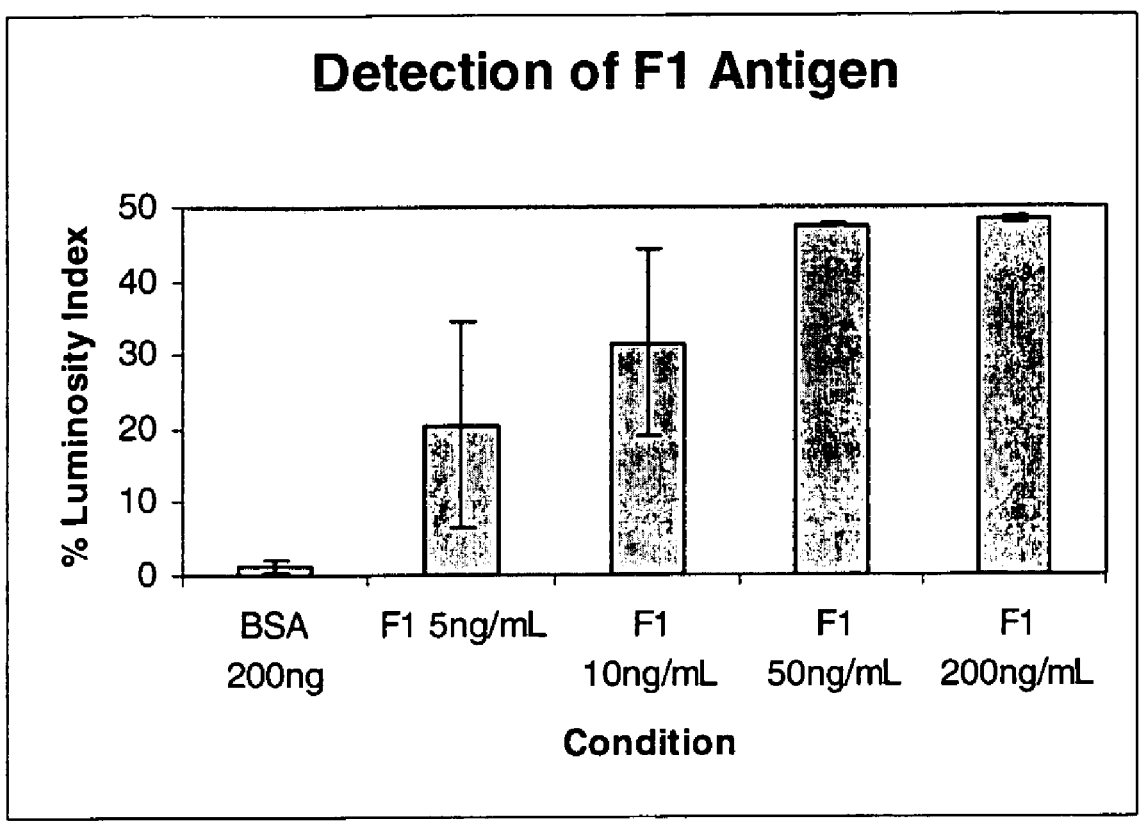
FIG. 2 is a graphic representation of luminosity index for the experiment depicted in FIG. 1.
Figure 3:
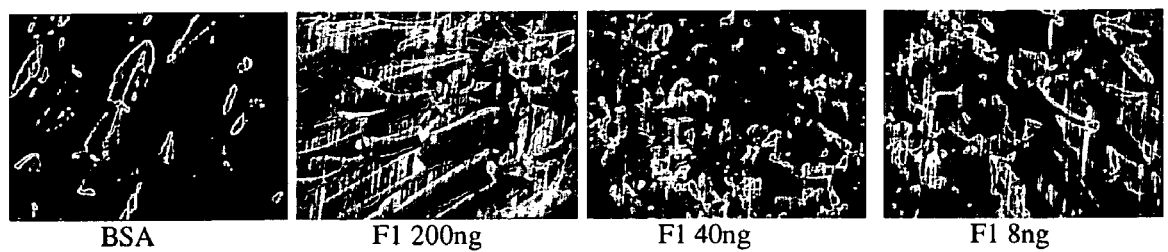
FIG. 3 is an image of an assay using a polyimide coated substrate to non-specifically detect an analyte.

As used herein, the term "recognition moiety" refers to a composition of matter that interacts with an analyte of interest in either a covalent or noncovalent manner.

As used herein, the term "virus recognition moiety" refers to any composition of matter that binds specifically to a virus. Examples of "virus recognition moieties" include, but are not limited to antigen binding proteins and nucleic acid aptamers.

The term "substrate" refers to a composition that serves as a base for another composition such as recognition moiety. Examples of substrates include, but are not limited to, silicon surfaces, glass surfaces, glass beads, magnetic beads, agarose beads, etc.

As used herein, the term "analyte" refers to a substance or chemical constituent that is undergoing analysis.

As used herein, the term "ligand" refers to any molecule that binds to or can be bound by another molecule. A ligand is any ion, molecule, molecular group, or other substance that binds to another entity to form a larger complex. Examples of ligands include, but are not limited to, peptides, carbohydrates, nucleic acids, antibodies, or any molecules that bind to receptors.

As used herein, the term "homeotropic director" refers to a topographical feature (e.g., a nanostructure or homeotropic orienting polyimide) of a substrate that homeotropically orients a liquid crystal.

As used herein, the term "pathogen" refers to disease causing organisms, microorganisms, or agents including, but not limited to, viruses, bacteria, parasites (including, but not limited to, organisms within the phyla Protozoa, Platyhelminthes, Aschelminthes, Acanthocephala, and Arthropoda), fungi, and prions.

As used herein, the term "bacteria" and "bacterium" refer to all prokaryotic organisms, including those within all of the phyla in the Kingdom Procaryotae. It is intended that the term encompass all microorganisms considered to be bacteria including Mycoplasma, Chlamydia, Actinomyces, Streptomyces, and Rickettsia. All forms of bacteria are included within this definition including cocci, bacilli, spirochetes, spheroplasts, protoplasts, etc. "Gram negative" and "gram positive" refer to staining patterns obtained with the Gram-staining process which is well known in the art (See e.g., Finegold and Martin, Diagnostic Microbiology, 6th Ed. (1982), C V Mosby St. Louis, pp 13-15).

As used herein, the term "lipid membrane" refers to, in its broadest sense, a thin sheet or layer comprising lipid molecules. It is intended that the term encompass all "biomembranes" (i.e., any organic membrane including, but not limited to, plasma membranes, nuclear membranes, organelle membranes, and synthetic membranes). Typically, membranes are composed of lipids, proteins, glycolipids, steroids, sterol and/or other components. As used herein, the term "membrane fragment" refers to any portion or piece of a membrane.

As used herein, the term "lipid" refers to a variety of compounds that are characterized by their solubility in organic solvents. Such compounds include, but are not limited to, fats, waxes, steroids, sterols, glycolipids, glycosphingolipids (including gangliosides), phospholipids, terpenes, fat-soluble vitamins, prostaglandins, carotenes, and chlorophylls. As used herein, the phrase "lipid-based materials" refers to any material that contains lipids.

As used herein, the term "liposome" refers to artificially produced spherical lipid complexes that can be induced to segregate out of aqueous media.

As used herein, the term "secondary binding agent" refer to a molecule or collection of molecules that binds to one of an analyte-recognition moiety complex. It is contemplated that secondary binding agents are useful for amplifying the signal resulting from analyte-recognition moiety binding.

As used herein, the term "column media" refers to media used to fill a chromatography column, such as cationic exchange media, anionic exchange media, and immunoaffinity column media.

As used herein, the term "detection region" refers to a discreet area on substrate that is designated for detection of an analyte (e.g., a virus of interest) in a sample.

As used herein, the term "immobilization" refers to the attachment or entrapment, either chemically or otherwise, of a material to another entity (e.g., a solid support) in a manner that restricts the movement of the material.

As used herein, the terms "material" and "materials" refer to, in their broadest sense, any composition of matter.

As used herein the term "antigen binding protein" refers to a glycoprotein evoked in an animal by an immunogen (antigen) and to proteins derived from such glycoprotein (e.g., single chain antibodies and F(ab')2, Fab' and Fab fragments). An antibody demonstrates specificity to the immunogen, or, more specifically, to one or more epitopes contained in the immunogen. Native antibody comprises at least two light polypeptide chains and at least two heavy polypeptide chains. Each of the heavy and light polypeptide chains contains at the amino terminal portion of the polypeptide chain a variable region (i.e., VH and VL respectively), which contains a binding domain that interacts with antigen. Each of the heavy and light polypeptide chains also comprises a constant region of the polypeptide chains (generally the carboxy terminal portion) which may mediate the binding of the immunoglobulin to host tissues or factors influencing various cells of the immune system, some phagocytic cells and the first component (C1q) of the classical complement system. The constant region of the light chains is referred to as the "CL region," and the constant region of the heavy chain is referred to as the "CH region." The constant region of the heavy chain comprises a CH1 region, a CH2 region, and a CH3 region. A portion of the heavy chain between the CH1 and CH2 regions is referred to as the hinge region (i.e., the "H region"). The constant region of the heavy chain of the cell surface form of an antibody further comprises a spacer-transmembranal region (M1) and a cytoplasmic region (M2) of the membrane carboxy terminus. The secreted form of an antibody generally lacks the M1 and M2 regions.

As used herein, the term "selective binding" refers to the binding of one material to another in a manner dependent upon the presence of a particular molecular structure (i.e., specific binding). For example, an immunoglobulin will selectively bind an antigen that contains the chemical structures complementary to the ligand binding site(s) of the immunoglobulin. This is in contrast to "non-selective binding," whereby interactions are arbitrary and not based on structural compatibilities of the molecules.

As used herein, the term "polymerization" encompasses any process that results in the conversion of small molecular monomers into larger molecules consisting of repeated units. Typically, polymerization involves chemical crosslinking of monomers to one another.

As used herein, the term "antigen" refers to any molecule or molecular group that is recognized by at least one antibody. By definition, an antigen must contain at least one epitope (i.e., the specific biochemical unit capable of being recognized by the antibody). The term "immunogen" refers to any molecule, compound, or aggregate that induces the production of antibodies. By definition, an immunogen must contain at least one epitope (i.e., the specific biochemical unit capable of causing an immune response).

As used herein, the terms "home testing" and "point of care testing" refer to testing that occurs outside of a laboratory environment. Such testing can occur indoors or outdoors at, for example, a private residence, a place of business, public or private land, in a vehicle, as well as at the patient's bedside.

As used herein, the term "virus" refers to minute infectious agents, which with certain exceptions, are not observable by light microscopy, lack independent metabolism, and are able to replicate only within a living host cell. The individual particles (i.e., virions) consist of nucleic acid and a protein shell or coat; some virions also have a lipid containing membrane. The term "virus" encompasses all types of viruses, including animal, plant, phage, and other viruses.

As used herein, term "nanostructures" refers to microscopic structures, typically measured on a nanometer scale. Such structures include various three-dimensional assemblies, including, but not limited to, liposomes, films, multilayers, braided, lamellar, helical, tubular, and fiber-like shapes, and combinations thereof. Such structures can, in some embodiments, exist as solvated polymers in aggregate forms such as rods and coils. Such structures can also be formed from inorganic materials, such as prepared by the physical deposition of a gold film onto the surface of a solid, proteins immobilized on surfaces that have been mechanically rubbed, and polymeric materials that have been molded or imprinted with topography by using a silicon template prepared by electron beam lithography.

As used herein, the terms "self-assembling monomers" and "lipid monomers" refer to molecules that spontaneously associate to form molecular assemblies. In one sense, this can refer to surfactant molecules that associate to form surfactant molecular assemblies. The term "self-assembling monomers" includes single molecules (e.g., a single lipid molecule) and small molecular assemblies (e.g., polymerized lipids), whereby the individual small molecular assemblies can be further aggregated (e.g., assembled and polymerized) into larger molecular assemblies.

As used herein, the term "linker" or "spacer molecule" refers to material that links one entity to another. In one sense, a molecule or molecular group can be a linker that is covalent attached two or more other molecules (e.g., linking a ligand to a self-assembling monomer).

As used herein, the term "bond" refers to the linkage between atoms in molecules and between ions and molecules in crystals. The term "single bond" refers to a bond with two electrons occupying the bonding orbital. Single bonds between atoms in molecular notations are represented by a single line drawn between two atoms (e.g., C—C). The term "double bond" refers to a bond that shares two electron pairs. Double bonds are stronger than single bonds and are more reactive. The term "triple bond" refers to the sharing of three electron pairs. As used herein, the term "ene-yne" refers to alternating double and triple bonds. As used herein the terms "amine bond," "thiol bond," and "aldehyde bond" refer to any bond formed between an amine group (i.e., a chemical group derived from ammonia by replacement of one or more of its hydrogen atoms by hydrocarbon groups), a thiol group (i.e., sulfur analogs of alcohols), and an aldehyde group (i.e., the chemical group —CHO joined directly onto another carbon atom), respectively, and another atom or molecule.

As used herein, the term "covalent bond" refers to the linkage of two atoms by the sharing of two electrons, one contributed by each of the atoms.

As used herein, the term "spectrum" refers to the distribution of light energies arranged in order of wavelength.

As used the term "visible spectrum" refers to light radiation that contains wavelengths from approximately 360 nm to approximately 800 nm.

As used herein, the term "substrate" refers to a solid object or surface upon which another material is layered or attached. Solid supports include, but are not limited to, glass, metals, gels, and filter paper, among others.

As used herein, the terms "array" and "patterned array" refer to an arrangement of elements (i.e., entities) into a material or device. For example, combining several types of ligand binding molecules (e.g., antibodies or nucleic acids) into an analyte-detecting device, would constitute an array.

As used herein, the term "in situ" refers to processes, events, objects, or information that are present or take place within the context of their natural environment.

As used herein, the term "sample" is used in its broadest sense. In one sense it can refer to a biopolymeric material. In another sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. These examples are not to be construed as limiting the sample types applicable to the present invention.

As used herein, the term "liquid crystal" refers to a thermodynamic stable phase characterized by anisotropy of properties without the existence of a three-dimensional crystal lattice, generally lying in the temperature range between the solid and isotropic liquid phase.

As used herein, the term "mesogen" refers to compound(s) that form liquid crystals, and in particular rigid rodlike or disclike molecules that are components of liquid crystalline materials.

As used herein, "thermotropic liquid crystal" refers to liquid crystals that result from the melting of mesogenic solids due to an increase in temperature. Both pure substances and mixtures form thermotropic liquid crystals.

"Lyotropic," as used herein, refers to molecules that form phases with orientational and/or positional order in a solvent. Lyotropic liquid crystals can be formed using amphiphilic molecules (e.g., sodium laurate, phosphatidylethanolamine, lecithin). The solvent can be water.

As used herein, the term "heterogenous surface" refers to a surface that orients liquid crystals in at least two separate planes or directions, such as across a gradient.

As used herein, "nematic" refers to liquid crystals in which the long axes of the molecules remain substantially parallel, but the positions of the centers of mass are randomly distributed. Nematic liquid crystals can be substantially oriented by a nearby surface.

"Chiral nematic," as used herein refers to liquid crystals in which the mesogens are optically active. Instead of the director being held locally constant as is the case for nematics, the director rotates in a helical fashion throughout the sample.

Chiral nematic crystals show a strong optical activity that is much higher than can be explained on the bases of the rotatory power of the individual mesogens. When light equal in wavelength to the pitch of the director impinges on the liquid crystal, the director acts like a diffraction grating, reflecting most and sometimes all of the light incident on it. If white light is incident on such a material, only one color of light is reflected and it is circularly polarized. This phenomenon is known as selective reflection and is responsible for the iridescent colors produced by chiral nematic crystals.

"Smectic," as used herein refers to liquid crystals which are distinguished from "nematics" by the presence of a greater degree of positional order in addition to orientational order; the molecules spend more time in planes and layers than they do between these planes and layers. "Polar smectic" layers occur when the mesogens have permanent dipole moments. In the smectic A2 phase, for example, successive layers show anti ferroelectric order, with the direction of the permanent dipole alternating from layer to layer. If the molecule contains a permanent dipole moment transverse to the long molecular axis, then the chiral smectic phase is ferroelectric. A device utilizing this phase can be intrinsically bistable.

"Frustrated phases," as used herein, refers to another class of phases formed by chiral molecules. These phases are not chiral, however, twist is introduced into the phase by an array of grain boundaries. A cubic lattice of defects (where the director is not defined) exist in a complicated, orientationally ordered twisted structure. The distance between these defects is hundreds of nanometers, so these phases reflect light just as crystals reflect x-rays.

"Discotic phases" are formed from molecules that are disc shaped rather than elongated. Usually these molecules have aromatic cores and six lateral substituents. If the molecules are chiral or a chiral dopant is added to a discotic liquid crystal, a chiral nematic discotic phase can form. "Viewed between crossed polarizers" means polarizers whose transmission axes are aligned at some angle.

"Polarizer" means a device, which in the transmission of electromagnetic radiation, confines the vibration of the electric and magnetic field vectors of light to one plane.

"Chamber" means any enclosed space. For example, a chamber may be, but not limited to, a tube made of glass or plastic.

"Pneumatic" means gaseous elements.

"Pneumatic gap" means a space of gaseous elements that separate two or more liquid compositions.

"Mesogen-aligning substrate" means a substrate that causes certain mesogens to align in a substantially similarly ordered direction in a liquid crystal when in contact with the substrate.

DESCRIPTION OF THE INVENTION

The present invention relates to the field of detection of analytes, and in particular to detection of viruses, cells, bacteria, lipid-membrane containing organisms, proteins, nucleic acids, carbohydrates and other biomolecules, organic molecules and inorganic molecules using a liquid crystal assay format. Liquid crystal-based assay systems (LC assays) are described in U.S. Pat. No. 6,284,197; WO 01/61357; WO 01/61325; WO 99/63329; Gupta et al., Science 279:2077-2080 (1998); Seung-Ryeol Kim, Rahul R. Shah, and Nicholas L. Abbott; Orientations of Liquid Crystals on Mechanically Rubbed Films of Bovine Serum Albumin: A Possible Substrate for Biomolecular Assays Based on Liquid Crystals, Analytical Chemistry; 2000; 72(19); 4646-4653; Justin J. Skaife and Nicholas L. Abbott; Quantitative Interpretation of the Optical Textures of Liquid Crystals Caused by Specific Binding of Immunoglobulins to Surface-Bound Antigens, Langmuir; 2000; 16(7); 3529-3536; Vinay K. Gupta and Nicholas L. Abbott; Using Droplets of Nematic Liquid Crystal To Probe the Microscopic and Mesoscopic Structure of Organic Surfaces, Langmuir; 1999; 15(21); 7213-7223; all of which are incorporated herein by reference.

The present invention provides systems, devices, and methods for both direct and indirect detection of analytes. The indirect detection systems utilize a first substrate comprising a recognition moiety that interacts with an analyte of interest, preferably specifically. After the first substrate is exposed to a sample suspected of containing an analyte, analyte interacting with the recognition moieties displayed on the first substrate are transferred to the second substrate. In preferred embodiments, the analyte interacts with the second substrate in a non-specific manner. In further preferred embodiments, the second substrate comprises a detection region that orients mesogens in liquid crystal. The second substrate is then contacted with a liquid crystal. A disordered liquid crystal is indicative of the presence of an analyte in the detection region.

The applicants do not intend the invention to be limited to any particular mechanism. But, the applicants believe that having a disordered liquid crystal indicates that some of the liquid crystal may contain mesophases that are not substantially aligned. In some liquid crystals, the birefringence is not constant over the entire sample surface. At times some of the mesogens manifest a perpendicular alignment while others manifest a planar alignment; therefore, some of the surface areas appear light and others appear dark when viewed between crossed polarizers. The light and dark areas denote regions of differing birefringence. The anisotropic nature of liquid crystals can be used to detect the presence of molecules. By way of nonlimiting examples, polyimide coated surfaces and polydimethylsiloxane (PDMS) [Dow Chemicals] micro fluidic channels align or can be made to align mesogens homeotropically (perpendicular to the surface). If a liquid crystal is fabricated on a sample polyimide surface (or PDMS micro fluidic channel) containing molecules on the sample surface, then the presence of the molecules between the mesogens and polyimide coating manifests itself by causing some planar alignment of the mesogens in the areas where the molecules interrupt homeotropic alignment form the polyimide surface. Thus, the presence of molecules on a spot (or in a micro fluidic channel) of the sample surface will result in areas of light appearance when the liquid crystal substrate is viewed between crossed polarizers.

WO 01/61357 describes the detection of viruses using liquid crystal based assays. These assays utilize a patterned detection region on a substrate that organizes mesogens in a homeotropic orientation. The assays are designed so that binding of a virus to the detection regions disrupts the homeotropic orientation.

The devices, systems and methods of the present invention are useful for detecting a variety of analytes, including, but not limited to, the following analytes: biomolecules including polypeptides (e.g., proteins), toxins, polynucleotides (e.g., RNA and DNA), carbohydrates, viruses, mycoplasmas, fungi, bacteria, and protozoa, especially Class A agents such as *Variola major* (smallpox), *Bacillus anthracis* (anthrax), *Yersinia pestis* (plague), *Clostridium botulinum* (botulism), *Francisella tularensis* (tularemia), Arenaviruses (Arenaviridae), Ebola hemorrhagic fever virus, Marburg hemorrhagic fever, Lassa fever virus, Junin and related viruses (Argentinian hemorrhagic fever virus, Bolivian hemorrhagic fever virus, Brazilian hemorrhagic fever virus, Venezuelan hemorrhagic fever virus), Dengue hemorrhagic fever virus, and toxins such as botulinum and Trichothecene (T2) mycotoxins; Class B agents such as *Coxiella burnetti* (Q fever), *Brucella* sp. (brucellosis), *Burkholderia mallei* (glanders), *Salmonella* sp., *Shigella dysenteria*, *Escherichia coli* strain O 157:H7, *Cryptosporidium parvum*, Alphaviruses (Togaviridae family) such as Venezuelan equine encephalitis virus, Eastern equine encephalitis virus, Western equine encephalitis virus, and toxins such as ricin toxin, epsilin toxin from *Clostridium perfigens*, and *Staphylococcus enterotoxin* B; and Class C agents such as mutlidrug resistant tuberculosis, Nipah virus, Hantaviruses, Tick-borne hemorrhagic fever viruses, Tick-borne encephalitis viruses, and Yellow fever virus. Other analytes include, but are not limited to, acids, bases, organic ions, inorganic ions, pharmaceuticals, herbicides, pesticides, chemical warfare agents, and noxious gases. These agents can be present as components in mixtures of structurally unrelated compounds, racemic mixtures of stereoisomers, non-racemic mixtures of stereoisomers, mixtures of diastereomers, mixtures of positional isomers or as pure compounds. The detection of these analytes, and specific substrates and recognition moieties for such detection, is described in more detail in co-pending application Ser. Nos. 10/227,974, 10/443,419, and 60/585,275; all of which are incorporated herein by reference in their entirety.

Accordingly, the present invention provides improved substrates and devices for the detection of analytes. For convenience, the description of the present invention is divided into the following sections: I. Recognition Moieties; II. Substrates; III. Functionalization of Substrates; IV. Mesogens; V. Direct Detection of Entities with Lipid Membranes; VI. Nonspecific Detection Following Specific Capture; VII. Detection with Lipid Tags VIII. Kits, and IX. Magnetic Beads in Fluidic Tubes.

I. Recognition Moieties

A variety of recognition moieties find use in the present invention. In preferred embodiments, the recognition moieties are immobilized on a bead, such as a magnetic bead. In some embodiments of the present invention, a "recognition moiety" attached to or associated with a bead is utilized to bind to or otherwise interact with another molecule or molecules (e.g., analytes). For example, in some embodiments, recognition moieties are attached to either ω-functionalized spacer arms or ω-functionalized SAM components which are in turn attached to or associated with a bead.

In some preferred embodiments, the recognition moiety comprises an organic functional group. In presently preferred embodiments, the organic functional group is a member selected from the group consisting of amines, carboxylic acids, drugs, chelating agents, crown ethers, cyclodextrins or a combination thereof. In another preferred embodiment, the recognition moiety is a biomolecule. In still further preferred embodiments, the biomolecule is a protein, antigen binding protein, peptide, nucleic acid (e.g., single nucleotides or nucleosides, oligonucleotides, polynucleotides and single- and higher-stranded nucleic acids) or a combination thereof. In a presently preferred embodiment, the recognition moiety is biotin. In some embodiments, the recognition moieties are antigen binding proteins. Examples of antigen binding proteins finding use in the present invention include, but are not limited to, immunoglobulins, single chain antibodies, chimeric antibodies, polyclonal antibodies, monoclonal antibodies, and F(ab')2, Fab' and Fab fragments.

Various procedures known in the art may be used for the production of polyclonal antibodies. For the production of antibody, various host animals, including but not limited to rabbits, mice, rats, sheep, goats, etc., can be immunized by injection with the peptide corresponding to an epitope. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

In addition, it is contemplated that techniques described for the production of single chain antibodies (U.S. Pat. No. 4,946, 778; herein incorporated by reference) will find use in producing specific single chain antibodies that serve as recognition moieties. Furthermore, it is contemplated that any technique suitable for producing antibody fragments will find use in generating antibody fragments that are useful recognition moieties. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent. In still further embodiments, the recognition moiety comprises a phage displaying an antigen binding protein.

In some embodiments where the recognition moiety is a polynucleotide or polypeptide, a plurality of recognition moieties are arrayed on the substrates using photo activated chemistry, microcontact printing, and ink-jet printing. In particularly preferred embodiments, photolithography is utilized (See e.g., U.S. Pat. Nos. 6,045,996; 5,925,525; and 5,858, 659; each of which is herein incorporated by reference). Using a series of photolithographic masks to define substrate exposure sites, followed by specific chemical synthesis steps, the process constructs high-density arrays of oligonucleotides, with each probe in a predefined position in the array. Multiple probe arrays are synthesized simultaneously on, for example, a large glass wafer. The wafers are then diced, and individual probe arrays are packaged in injection-molded plastic cartridges, which protect them from the environment and serve as chambers for hybridization.

In other embodiments, nucleic acid recognition moieties are electronically captured on a suitable substrate (See e.g., U.S. Pat. Nos. 6,017,696; 6,068,818; and 6,051,380; each of which are herein incorporated by reference). Through the use of microelectronics, this technology enables the active movement and concentration of charged molecules to and from designated test sites on its semiconductor microchip. DNA capture probes unique to a given target are electronically placed at, or "addressed" to, specific sites on the microchip.

Since DNA has a strong negative charge, it can be electronically moved to an area of positive charge.

In still further embodiments, recognition moieties are arrayed on a suitable substrate by utilizing differences in surface tension (See e.g., U.S. Pat. Nos. 6,001,311; 5,985,551; and 5,474,796; each of which is herein incorporated by reference). This technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

In still further embodiments, recognition moieties are spotted onto a suitable substrate. Such spotting can be done by hand with a capillary tube or micropipette, or by an automated spotting apparatus such as those available from Affymetrix and Gilson (See e.g., U.S. Pat. Nos. 5,601,980; 6,242,266; 6,040,193; and 5,700,637; each of which is incorporated herein by reference).

When the recognition moiety is an amine, in preferred embodiments, the recognition moiety will interact with a structure on the analyte which reacts by binding to the amine (e.g., carbonyl groups, alkylhalo groups). In another preferred embodiment, the amine is protonated by an acidic moiety on the analyte of interest (e.g., carboxylic acid, sulfonic acid).

In certain preferred embodiments, when the recognition moiety is a carboxylic acid, the recognition moiety will interact with the analyte by complexation (e.g., metal ions). In still other preferred embodiments, the carboxylic acid will protonate a basic group on the analyte (e.g. amine).

In another preferred embodiment, the recognition moiety is a drug moiety. The drug moieties can be agents already accepted for clinical use or they can be drugs whose use is experimental, or whose activity or mechanism of action is under investigation. The drug moieties can have a proven action in a given disease state or can be only hypothesized to show desirable action in a given disease state. In a preferred embodiment, the drug moieties are compounds that are being screened for their ability to interact with an analyte of choice. As such, drug moieties that are useful in practicing the instant invention include drugs from a broad range of drug classes having a variety of pharmacological activities.

Classes of useful agents include, for example, non-steroidal anti-inflammatory drugs (NSAIDS). The MAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniranune, triprolidine); antitussive drugs (e.g., dextromethorphan, codeine, carmiphen and carbetapentane); antipruritic drugs (e.g., methidilizine and trimeprizine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyraminde, quinidine, encainide); P-adrenergic blocker drugs (e.g., metoprolol, acebutolol, betaxolol, labetalol and timolol); cardiotonic drugs (e.g., milrinone, amrinone and dobutamine); antihypertensive drugs (e.g., enalapril, clonidine, hydralazine, minoxidil, guanadrel, guanethidine); diuretic drugs (e.g., amiloride and hydrochlorothiazide); vasodilator drugs (e.g., diltazem, amiodarone, isosuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chlorprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazepam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole; pentamidine, gentamycin, kanamycin, lineomycin, methacycline, methenamine, minocycline, neomycin, netilmycin, paromomycin, streptomycin, tobramycin, miconazole, and amanfadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, a-2-interferon) anti-estrogens (e.g., tamoxifen), antimetabolites (e.g., fluorouracil, methotrexate, mercaptopurine, thioguanine).

The recognition moiety can also comprise hormones (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, dephenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progenstogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful recognition moieties include immunomodulating drugs (e.g., antihistamines, mast cell stabilizers, such as Iodoxamide and/or cromolyn, steroids (e.g., triamcinolone, beclomethazone, cortisone, dexamethasone, prednisolone, methylprednisolone, beclomethasone, or clobetasol), histamine $H_2$ antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

When the recognition moiety is a chelating agent, crown ether or cyclodextrin, host-guest chemistry will dominate the interaction between the recognition moiety and the analyte. The use of host-guest chemistry allows a great degree of recognition-moiety-analyte specificity to be engineered into a device of the invention. The use of these compounds to bind to specific compounds is well known to those of skill in the art. See, for example, Pitt et al. "The Design of Chelating Agents for the Treatment of Iron Overload," In, INORGANIC CHEMISTRY IN BIOLOGY AND MEDICINE; Martell, A. E., Ed.; American Chemical Society, Washington, D.C., 1980, pp. 279-312; Lindoy, L. F., THE CHEMISTRY OF MACROCYCLIC LIGAND COMPLEXES; Cambridge University Press, Cambridge, 1989; Dugas, H., BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, R. E., Whitaker, 1.R., Eds., American Chemical Society, Washington, D.C., 1982, pp. 370-387; Kasina et al. *Bioconjugate Chem.* 9:108-117 (1998); Song et al., *Bioconjugate Chem.* 8:249-255 (1997).

In a presently preferred embodiment, the recognition moiety is a polyaminocarboxylate chelating agent such as ethylenediaminetetraacetic acid (EDTA) or diethylenetriaminepentaacetic acid (DTPA). These recognition moieties can be attached to any amine-terminated component of a SAM or a spacer arm, for example, by utilizing the commercially available dianhydride (Aldrich Chemical Co., Milwaukee, Wis.).

In still further preferred embodiments, the recognition moiety is a biomolecule such as a protein, nucleic acid, peptide or an antibody. Biomolecules useful in practicing the present invention can be derived from any source. The biomolecules can be isolated from natural sources or can be produced by synthetic methods. Proteins can be natural proteins or mutated proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal. Peptides and nucleic acids can be isolated from natural sources or can be wholly or partially synthetic in origin.

In those embodiments wherein the recognition moiety is a protein or antibody, the protein can be tethered to a SAM component or a spacer arm by any reactive peptide residue available on the surface of the protein. In preferred embodiments, the reactive groups are amines or carboxylates. In particularly preferred embodiments, the reactive groups are the e-amine groups of lysine residues. Furthermore, these molecules can be adsorbed onto the surface of the substrate or SAM by non-specific interactions (e.g., chemisorption, physisorption).

Recognition moieties that are antibodies can be used to recognize analytes which are proteins, peptides, nucleic acids, saccharides or small molecules such as drugs, herbicides, pesticides, industrial chemicals and agents of war. Methods of raising antibodies for specific molecules are well-known to those of skill in the art. See, U.S. Pat. Nos. 5,147,786; 5,334,528; 5,686,237; 5,573,922; each of which is incorporated herein by reference. Methods for attaching antibodies to surfaces are also art-known (See, Delamarche et al. *Langmuir* 12:1944-1946 (1996)).

Peptides and nucleic acids can be attached to a SAM component or spacer arm. Both naturally-derived and synthetic peptides and nucleic acids are of use in conjunction with the present invention. These molecules can be attached to a SAM component or spacer arm by any available reactive group. For example, peptides can be attached through an amine, carboxyl, sulfhydryl, or hydroxyl group. Such a group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain (See, Chrisey et al. *Nucleic Acids Res.* 24:3031-3039 (1996)).

When the peptide or nucleic acid is a fully or partially synthetic molecule, a reactive group or masked reactive group can be incorporated during the process of the synthesis. Many derivatized monomers appropriate for reactive group incorporation in both peptides and nucleic acids are know to those of skill in the art (See, for example, THE PEPTIDES: ANALYSIS, SYNTHESIS, BIOLOGY, Vol. 2: "Special Methods in Peptide Synthesis," Gross, E. and Melenhofer, J., Eds., Academic Press, New York (1980)). Many useful monomers are commercially available (Bachem, Sigma, etc.). This masked group can then be unmasked following the synthesis, at which time it becomes available for reaction with a SAM component or a spacer arm.

In other preferred embodiments, the peptide is attached directly to the substrate (See, Frey et al. *Anal. Chem.* 68:3187-3193 (1996)). In a particularly preferred embodiment, the peptide is attached to a gold substrate through a sulfhydryl group on a cysteine residue. In another preferred embodiment, the peptide is attached through a thiol to a spacer arm which terminates in, for example, an iodoacetamide, chloroacetamide, benzyl iodide, benzyl bromide, alkyl iodide or alkyl bromide. Similar immobilization techniques are known to those of skill in the art (See, for example, Zull et al. *J. Ind Microbiol.* 13:137-143 (1994)).

In another preferred embodiment, the recognition moiety forms an inclusion complex with the analyte of interest. In a particularly preferred embodiment, the recognition moiety is a cyclodextrin or modified cyclodextrin. Cyclodextrins are a group of cyclic oligosaccharides produced by numerous microorganisms. Cyclodextrins have a ring structure which has a basket-like shape. This shape allows cyclodextrins to include many kinds of molecules into their internal cavity (See, for example, Szejtli, J., CYCLODEXTRINS AND THEIR INCLUSION COMPLEXES; Akademiai Klado, Budapest, 1982; and Bender et al., CYCLODEXTRIN CHEMISTRY, Springer-Verlag, Berlin, 1978). Cyclodextrins are able to form inclusion complexes with an array of organic molecules including, for example, drugs, pesticides, herbicides and agents of war (See, Tenjarla et al., *J. Pharm. Sci.* 87:425-429 (1998); Zughul et al., *Pharm. Dev. Technol.* 3:43-53 (1998); and Albers et al., *Crit. Rev. Ther. Drug Carrier Syst.* 12:311-337 (1995)). Importantly, cyclodextrins are able to discriminate between enantiomers of compounds in their inclusion complexes. Thus, in one preferred embodiment, the invention provides for the detection of a particular enantiomer in a mixture of enantiomers (See, Koppenhoefer et al. *J. Chromatogr. A* 793:153-164 (1998)).

The cyclodextrin recognition moiety can be attached to a SAM component, through a spacer arm or directly to the substrate (See, Yamamoto et al., *J. Phys. Chem. B* 101:6855-6860 (1997)). Methods to attach cyclodextrins to other molecules are well known to those of skill in the chromatographic and pharmaceutical arts (See, Sreenivasan, *Appl. Polym. Sci.* 60:2245-2249 (1996)).

In other embodiments, the recognition moieties can be nucleic acids (e.g., RNA or DNA) or receptors that are specific for a particular entity (e.g., virus). In some embodiments, the nucleic acids are aptamers. The isolation of aptamers is described in U.S. Pat. Nos. 5,475,096; 5,270,163; and 5,475,096; and in PCT publications WO 97/38134, WO 98/33941, and WO 99/07724, all of which are herein incorporated by reference.

In some embodiments, recognition moieties are incorporated to detect a variety of bacteria and pathogens. Such recognition moieties include, but not limited to, sialic acid to detect HIV (Wies et al., Nature 333: 426 [1988]), influenza (White et al., Cell 56: 725 [1989]), chlamydia (Infect. Imm. 57: 2378 [1989]), reovirus, *Streptococcus suis, Salmonella,* Sendai virus, mumps, newcastle, myxovirus, and *Neisseria meningitidis;* 9-OAC sialic acid to detect coronavirus, encephalomyelitis virus, and rotavirus; non-sialic acid glycoproteins to detect cytomegalovirus (Virology 176: 337 [1990]) and measles virus (Virology 172: 386 [1989]); CD4 (Khatzman et al., Nature 312: 763 [1985]), vasoactive intestinal peptide (Sacerdote et al., J. of Neuroscience Research 18: 102 [1987]), and peptide T (Ruff et al., FEBS Letters 211: 17 [1987]) to detect HIV; epidermal growth factor to detect vaccinia (Epstein et al., Nature 318: 663 [1985]); acetylcholine receptor to detect rabies (Lentz et al., Science 215: 182 [1982]); Cd3 complement receptor to detect Epstein-Barr virus (Carel et al., J. Biol. Chem. 265: 12293 [1990]); β-adrenergic receptor to detect rheovirus (Co et al., Proc. Natl. Acad. Sci. 82: 1494 [1985]); ICAM-1 (Marlin et al., Nature 344: 70 [1990]), N-CAM, and myelin-associated glycoprotein MAb (Shephey et al., Proc. Natl. Acad. Sci. 85: 7743 [1988]) to detect rhinovirus; polio virus receptor to detect polio virus (Mendelsohn et al., Cell 56: 855 [1989]); fibroblast growth factor receptor to detect herpesvirus (Kaner et al., Science 248: 1410 [1990]); oligomannose to detect *Escherichia coli*; ganglioside $G_M1$ to detect *Neisseria meningitidis*; and antibodies to detect a broad variety of pathogens (e.g., *Neisseria gonorrhoeae, V. vulnificus, V. parahaemolyticus, V. cholerae, V. alginolyticus,* etc.).

In still further embodiments, the recognition moiety is a ligand that interacts with a binding partner. Examples of ligands include, but are not limited to, small organic molecules such as steroid molecules and small drug molecules, proteins, polypeptides and peptides, metal ions, and nucleic acids. In some embodiments, the ligand is recognized by a binding molecule in a sample. Examples of binding molecules include, but are not limited to, steroids, hormones, proteins, polypeptides, and peptides such immunoglobulin molecules and fragments thereof, nucleic acids, and other organic or non-organic molecules. In some preferred embodiments, the ligand is recognized by a binding molecule in a body fluid of a test subject. For example, the ligand can be a virus envelope protein or some other antigenic molecule from a pathogenic organism (such as those listed above). In preferred embodiments, the antigenic molecule (e.g., a protein) is recognized by an antibody molecule in the body fluid of a test subject that has been exposed to the pathogenic organism. In particularly preferred embodiments, the ligand is protein E from the envelope of West Nile Virus.

II. Substrates

Substrates that are useful in practicing the present invention can be made of practically any physicochemically stable material. In some embodiments, the recognitions moieties are attached to a first substrate (such as a bead), but detection with the liquid crystal occurs after transfer to a second substrate (e.g., a detection substrate). In a preferred embodiment, the substrate material is non-reactive towards the constituents of the mesogenic layer. The substrates can be either rigid or flexible and can be either optically transparent or optically opaque. The substrates can be electrical insulators, conductors or semiconductors. Further, the substrates can be substantially impermeable to liquids, vapors and/or gases or, alternatively, the substrates can be permeable to one or more of these classes of materials. Exemplary substrate materials include, but are not limited to, inorganic crystals, inorganic glasses, inorganic oxides, metals, organic polymers and combinations thereof. In some embodiments, the substrates have microchannels therein for the delivery of sample and/or other reagents to the substrate surface or detection regions thereon. The design and use of microchannels are described, for example, in U.S. Pat. Nos. 6,425,972, 6,418,968, 6,447,727, 6,432,720, 5,976,336, 5,882,465, 5,876,675, 6,186,660, 6,100,541, 6,379,974, 6,267,858, 6,251,343, 6,238,538, 6,182,733, 6,068,752, 6,429,025, 6,413,782, 6,274,089, 6,150,180, 6,046,056, 6,358,387, 6,321,791, 6,326,083, 6,171,067, and 6,167,910, all of which are incorporated herein by reference.

A. Inorganic Crystal and Glasses

In some embodiments of the present invention, inorganic crystals and inorganic glasses are utilized as substrate materials (e.g., LiF, NaF, NaCl, KBr, KI, $CaF_2$, $MgF_2$, $HgF_2$, BN, $AsS_3$, ZnS, $Si_3N_4$ and the like). The crystals and glasses can be prepared by art standard techniques (See, e.g., Goodman, C. H. L., Crystal Growth Theory and Techniques, Plenum Press, New York 1974). Alternatively, the crystals can be purchased commercially (e.g., Fischer Scientific). The crystals can be the sole component of the substrate or they can be coated with one or more additional substrate components. Thus, it is within the scope of the present invention to utilize crystals coated with, for example one or more metal films or a metal film and an organic polymer. Additionally, a crystal can constitute a portion of a substrate which contacts another portion of the substrate made of a different material, or a different physical form (e.g., a glass) of the same material. Other useful substrate configurations utilizing inorganic crystals and/or glasses will be apparent to those of skill in the art.

B. Inorganic Oxides

In other embodiments of the present invention, inorganic oxides are utilized as the substrate. Inorganic oxides of use in the present invention include, for example, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), quartz, $In_2O_3$, $SnO_2$, $PbO_2$ and the like. The inorganic oxides can be utilized in a variety of physical forms such as films, supported powders, glasses, crystals and the like. A substrate can consist of a single inorganic oxide or a composite of more than one inorganic oxide. For example, a composite of inorganic oxides can have a layered structure (i.e., a second oxide deposited on a first oxide) or two or more oxides can be arranged in a contiguous non-layered structure. In addition, one or more oxides can be admixed as particles of various sizes and deposited on a support such as a glass or metal sheet. Further, a layer of one or more inorganic oxides can be intercalated between two other substrate layers (e.g., metal-oxide-metal, metal-oxide-crystal).

In a presently preferred embodiment, the substrate is a rigid structure that is impermeable to liquids and gases. In this embodiment, the substrate consists of a glass plate onto which a metal, such as gold is layered by evaporative deposition. In a still further preferred embodiment, the substrate is a glass plate ($SiO_2$) onto which a first metal layer such as titanium has been layered. A layer of a second metal such as gold is then layered on top of the first metal layer.

C. Metals

In still further embodiments of the present invention, metals are utilized as substrates. The metal can be used as a crystal, a sheet or a powder. The metal can be deposited onto a backing by any method known to those of skill in the art including, but not limited to, evaporative deposition, sputtering, electroless deposition, electrolytic deposition and adsorption or deposition of preform particles of the metal including metallic nanoparticles.

Any metal that is chemically inert towards the mesogenic layer will be useful as a substrate in the present invention. Metals that are reactive or interactive towards the mesogenic layer will also be useful in the present invention. Metals that are presently preferred as substrates include, but are not limited to, gold, silver, platinum, palladium, nickel and copper. In one embodiment, more than one metal is used. The more than one metal can be present as an alloy or they can be formed into a layered "sandwich" structure, or they can be laterally adjacent to one another. In a preferred embodiment, the metal used for the substrate is gold. In a particularly preferred embodiment the metal used is gold layered on titanium.

The metal layers can be either permeable or impermeable to materials such as liquids, solutions, vapors and gases.

D. Organic Polymers

In still other embodiments of the present invention, organic polymers are utilized as substrate materials. Organic polymers useful as substrates in the present invention include polymers that are permeable to gases, liquids and molecules in solution. Other useful polymers are those that are impermeable to one or more of these same classes of compounds.

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysilanes, fluorinated polymers, epoxies, polyethers and phenolic resins (See, Cognard, J. ALIGNMENT OF NEMATIC LIQUID CRYSTALS AND THEIR MIXTURES, in Mol. Cryst. Liq. Cryst. 1:1-74 (1982)). Presently preferred organic polymers include polydimethylsiloxane, polyethylene, polyacrylonitrile, cellulosic materials, polycarbonates and polyvinyl pyridinium.

In a presently preferred embodiment, the substrate is permeable and it consists of a layer of gold, or gold over titanium, which is deposited on a polymeric membrane, or other material, that is permeable to liquids, vapors and/or gases. The liquids and gases can be pure compounds (e.g., chloroform, carbon monoxide) or they can be compounds which are dispersed in other molecules (e.g., aqueous protein solutions, herbicides in air, alcoholic solutions of small organic molecules). Useful permeable membranes include, but are not limited to, flexible cellulosic materials (e.g., regenerated cellulose dialysis membranes), rigid cellulosic materials (e.g., cellulose ester dialysis membranes), rigid polyvinylidene fluoride membranes, polydimethylsiloxane and track etched polycarbonate membranes.

In a further preferred embodiment, the layer of gold on the permeable membrane is itself permeable. In a still further preferred embodiment, the permeable gold layer has a thickness of about 70 Angstroms or less.

In those embodiments wherein the permeability of the substrate is not a concern and a layer of a metal film is used, the film can be as thick as is necessary for a particular application. For example, if the film is used as an electrode, the film can be thicker than in an embodiment in which it is necessary for the film to be transparent or semi-transparent to light.

Thus, in a preferred embodiment, the film is of a thickness of from about 0.01 nanometer to about 1 micrometer. In a further preferred embodiment, the film is of a thickness of from about 5 nanometers to about 100 nanometers. In yet a further preferred embodiment, the film is of a thickness of from about 10 nanometers to about 50 nanometers.

E. Multi-Substrate Systems

As described above, in some embodiments a first substrate (e.g., a capture substrate such as a bead) is functionalized with a recognition moiety that binds an analyte that is subsequently transferred to a second substrate (e.g., a detection substrate). In embodiments where two or more substrates are utilized, the two or more substrates may comprise any of the materials described above. The first substrates of the present invention are provided in a variety of formats. In some embodiments, the first substrate is a stamp. In preferred embodiments, the stamp comprises a plurality of analyte binding regions that display recognition moieties. In some particularly preferred embodiments, the analyte binding regions are extensions from the body of the stamp. Stamps of the present invention are not limited to any particular material composition. In some preferred embodiments, the stamps are formed from a pliable material, such as PDMS. In other embodiments, the first substrates may present planar or curved surfaces or be beads. The bead format is especially useful for the indirect detection methods described below. The bead substrates of the present invention may comprise any of the substrate materials described above. In some preferred embodiments, the beads are commercially available beads such as agarose beads, acrylic beads, or latex beads. In some embodiments, the beads are magnetic. In still other embodiments, the beads are coated with a metal such as silver or gold. In still other embodiments, substrates such column chromatography media may be used to capture analytes. Examples of such substrates include immunoaffinity columns (i.e., columns containing media functionalized with antigen binding proteins), protein-A affinity columns, cation exchange columns such as S-SEPHAROSE, SP-SEPHAROSE, and carboxymethyl cellulose, anion exchange columns such as DEAE Cellulose, QAE SEPHADEX, and FAST Q SEPHAROSE, sizing columns such as ULTRAGEL columns, phsosphocelluse columns, heparin sulfate columns, and the like. Following elution for the columns analytes are detected as described in detail below.

III. Functionalization of Substrates

In some embodiments, the surface of the substrate (e.g., a first or second substrate as described above) is functionalized so that a recognition moiety is immobilized on the surface of the substrate. In some embodiments, the immobilized recognition moiety forms a detection region. In some embodiments, a plurality of detection regions are formed on the surface of the substrate. In some embodiments, the same recognition moiety is provided on two or more of the plurality of detection regions, while in other embodiments, at least two different recognition moieties are immobilized on one or more of the plurality of detection regions. In some embodiments, the recognition moieties are arrayed in discreet detection regions on the substrate surfaces by the methods described in more detail below.

A. Self-Assembled Monolayers

In some embodiments, the surface of the substrate is first functionalized by forming a self-assembled monolayer (SAM) on the substrate surface. Self-assembled monolayers are generally depicted as an assembly of organized, closely packed linear molecules. There are two widely-used methods to deposit molecular monolayers on solid substrates: Langmuir-Blodgett transfer and self-assembly. Additional methods include techniques such as depositing a vapor of the monolayer precursor onto a substrate surface and the layer-by-layer deposition of polymers and polyelectrolytes from solution (Ladam et al., Protein Adsorption onto Auto-Assembled Polyelectrolyte Films, Langmuir; 2001; 17(3); 878-882).

The composition of a layer of a SAM useful in the present invention can be varied over a wide range of compound structures and molar ratios. In one embodiment, the SAM is formed from only one compound. In a presently preferred embodiment, the SAM is formed from two or more components. In another preferred embodiment, when two or more components are used, one component is a long-chain hydrocarbon having a chain length of between 10 and 25 carbons and a second component is a short-chain hydrocarbon having a chain length of between 1 and 9 carbon atoms. In particularly preferred embodiments, the SAM is formed from $CH_3(CH_2)_{15}SH$ and $CH_3(CH_2)_4SH$ or $CH_3(CH_2)_{15}SH$ and $CH_3(CH_2)_9SH$. In any of the above described embodiments, the carbon chains can be functionalized at the ω-terminus (e.g., $NH_2$, COOH, OH, CN), at internal positions of the chain (e.g., aza, oxa, thia) or at both the ω-terminus and internal positions of the chain.

A recognition moiety can be attached to the surface of a SAM by any of a large number of art-known attachment methods. In one preferred embodiment, a reactive SAM component is attached to the substrate and the recognition moiety is subsequently bound to the SAM component via the reactive group on the component and a group of complementary reactivity on the recognition moiety (See, e.g., Hegner et al. Biophys. J. 70:2052-2066 (1996)). In another preferred embodiment, the recognition moiety is attached to the SAM component prior to immobilizing the SAM component on the substrate surface: the recognition moiety-SAM component cassette is then attached to the substrate. In a still further preferred embodiment, the recognition moiety is attached to the substrate via a displacement reaction. In this embodiment, the SAM is preformed and then a fraction of the SAM components are displaced by a recognition moiety or a SAM component bearing a virus recognition moiety. In still other embodiments, the polypeptide recognition moieties are adsorbed directly onto hydrophobic monolayers such as $CH_3(CH_2)_{15}SH$. In embodiments where the recognition moiety is an antibody or other molecule that binds to protein A, protein A is first attached to the monolayer followed by the antibody, which is bound by protein A.

B. Functionalized SAMs

The discussion which follows focuses on the attachment of a reactive SAM component to the substrate surface. This focus is for convenience only and one of skill in the art will understand that the discussion is equally applicable to embodiments in which the SAM component-recognition moiety is preformed prior to its attachment to the substrate. As used herein, "reactive SAM components" refers to components that have a functional group available for reaction with a recognition moiety or other species following the attachment of the component to the substrate.

Currently favored classes of reactions available with reactive SAM components are those that proceed under relatively mild conditions. These include, but are not limited to nucleophilic substitutions (e.g., reactions of amines and alcohols with acyl halides), electrophilic substitutions (e.g., enamine reactions) and additions to carbon-carbon and carbon-heteroatom multiple bonds (e.g., Michael reaction, Diels-Alder addition). These and other useful reactions are discussed in March, ADVANCED ORGANIC CHEMISTRY, Third Ed., John Wiley & Sons, New York, 1985.

According to the present invention, a substrate's surface is functionalized with SAM, components and other species by covalently binding a reactive SAM component to the substrate surface in such a way as to derivatize the substrate surface with a plurality of available reactive functional groups. Reactive groups which can be used in practicing the present invention include, for example, amines, hydroxyl groups, carboxylic acids, carboxylic acid derivatives, alkenes, sulfhydryls, siloxanes, etc.

A wide variety of reaction types are available for the functionalization of a substrate surface. For example, substrates constructed of a plastic such as polypropylene, can be surface derivatized by chromic acid oxidation, and subsequently converted to hydroxylated or aminomethylated surfaces. Substrates made from highly crosslinked divinylbenzene can be surface derivatized by chloromethylation and subsequent functional group manipulation. Additionally, functionalized substrates can be made from etched, reduced polytetrafluoroethylene.

When the substrates are constructed of a siliaceous material such as glass, the surface can be derivatized by reacting the surface Si—OH, Si0-H, and/or Si—Si groups with a functionalizing reagent. When the substrate is made of a metal film, the surface can be derivatized with a material displaying avidity for that metal.

In a preferred embodiment, wherein the substrates are made from glass, the covalent bonding of the reactive group to the glass surface is achieved by conversion of groups on the substrate's surface by a silicon modifying reagent such as:

$$(RO)_3-Si-R^1-X^1 \tag{1}$$

where R is an alkyl group, such as methyl or ethyl, $R^1$ is a linking group between silicon and X and X is a reactive group or a protected reactive group. The reactive group can also be a recognition moiety as discussed below. Silane derivatives having halogens or other leaving groups beside the displayed alkoxy groups are also useful in the present invention.

A number of siloxane functionalizing reagents can be used, for example:
1. Hydroxyalkyl siloxanes (Silylate surface, functionalize with diborane, and $H_2O_2$ to oxidize the alcohol)
    a. allyl trichlorosilane→→3-hydroxypropyl
    b. 7-oct-1-enyl trichlorosilane→→8-hydroxyoctyl
2. Diol (dihydroxyalkyl) siloxanes (silylate surface and hydrolyze to diol)
    a. (glycidyl trimethoxysilane→→(2,3-dihydroxypropyloxy)propyl
3. Aminoalkyl siloxanes (amines requiring no intermediate functionalizing step).
    a. 3-aminopropyl trimethoxysilane→aminopropyl
4. Dimeric secondary aminoalkyl siloxanes
    a. bis (3-trimethoxysilylpropyl) amine→bis(silyloxylpropyl)amine.

It will be apparent to those of skill in the art that an array of similarly useful functionalizing chemistries are available when SAM components other than siloxanes are used. Thus, for example similarly functionalized alkyl thiols can be attached to metal films and subsequently reacted to produce the functional groups such as those exemplified above.

In another preferred embodiment, the substrate is at least partially a metal film, such as a gold film, and the reactive group is tethered to the metal surface by an agent displaying avidity for that surface. In a presently preferred embodiment, the substrate is at least partially a gold film and the group which reacts with the metal surface comprises a thiol, sulfide or disulfide such as:

$$Y\text{—}S\text{—}R^2\text{—}X^2 \tag{2}$$

$R^2$ is a linking group between sulfur and $X^2$ and $X^2$ is a reactive group or a protected reactive group. $X^2$ can also be a recognition moiety as discussed below. Y is a member selected from the group consisting of H, $R^3$ and $R^3$—S—, wherein $R^2$ and $R^3$ are independently selected. When $R^2$ and $R^3$ are the same, symmetrical sulfides and disulfides result, and when they are different, asymmetrical sulfides and disulfides result. A large number of functionalized thiols, sulfides and disulfides are commercially available (Aldrich Chemical Co., St. Louis). Additionally, those of skill in the art have available to them a manifold of synthetic routes with which to produce additional such molecules. For example, amine-functionalized thiols can be produced from the corresponding halo-amines, halo-carboxylic acids, etc. by reaction of these halo precursors with sodium sulfhydride. See, e.g., Reid, ORGANIC CHEMISTRY of BIVALENT SULFUR, VOL 1, pp. 21-29, 32-35, vol. 5, pp. 27-34, Chemical Publishing Co., New York, 1.958, 1963. Additionally, functionalized sulfides can be prepared via alkylthio-de-halogenation with a mercaptan salt (See, Reid, ORGANIC CHEMISTRY OF BIVALENT SULFUR, vol. 2, pp. 16-21, 24-29, vol. 3, pp. 11-14, Chemical Publishing Co., New York, 1960). Other methods for producing compounds useful in practicing the present invention will be apparent to those of skill in the art.

In another preferred embodiment, the functionalizing reagent provides for more than one reactive group per each reagent molecule. Using reagents such as Compound 3, below, each reactive site on the substrate surface is, in essence, "amplified" to two or more functional groups:

$$(RO)_3\text{—}Si\text{—}R^2\text{—}(X^2)_n \tag{3}$$

where R is an alkyl group, such as methyl, $R^2$ is a linking group between silicon and $X^2$, $X^2$ is a reactive group or a protected reactive group and n is an integer between 2 and 50, and more preferably between 2 and 20.

Similar amplifying molecules are also of use in those embodiments wherein the substrate is at least partially a metal film. In these embodiments the group which reacts with the metal surface comprises a thiol, sulfide or disulfide such as in Formula (4):

$$Y\text{—}S\text{—}R^2\text{—}(X^2)_n \tag{4}$$

As discussed above, $R^2$ is a linking group between sulfur and $X^2$ and $X^2$ is a reactive group or a protected reactive group. $X^2$ can also be a recognition moiety. Y is a member selected from the group consisting of H, $R^3$ and $R^3$—S—, wherein $R^2$ and $R^3$ are independently selected.

R groups of use for $R^1$, $R^2$ and $R^3$ in the above described embodiments of the present invention include, but are not limited to, alkyl, substituted alkyl, aryl, arylalkyl, substituted aryl, substituted arylalkyl, acyl, halogen, hydroxy, amino, alkylamino, acylamino, alkoxy, acyloxy, aryloxy, aryloxy-alkyl, mercapto, saturated cyclic hydrocarbon, unsaturated cyclic hydrocarbon, heteroaryl, heteroarylalkyl, substituted heteroaryl, substituted heteroarylalkyl, heterocyclic, substituted heterocyclic and heterocyclicalkyl groups.

In each of Formulae 1-4, above, each of $R^1$, $R^2$ and $R^3$ are either stable or they can be cleaved by chemical or photochemical reactions. For example, R groups comprising ester or disulfide bonds can be cleaved by hydrolysis and reduction, respectively. Also within the scope of the present invention is the use of R groups which are cleaved by light such as, for example, nitrobenzyl derivatives, phenacyl groups, benzoin esters, etc. Other such cleaveable groups are well-known to those of skill in the art.

In another preferred embodiment, the organosulfur compound is partially or entirely halogenated. An example of compounds useful in this embodiment include:

$$X^1Q_2C(CQ^1{}_2)_mZ^1(CQ^2{}_2)_nSH \tag{5}$$

wherein, $X^1$ is a member selected from the group consisting of H, halogen reactive groups and protected reactive groups. Reactive groups can also be recognition moieties as discussed below. Q, $Q^1$ and $Q^2$ are independently members selected from the group consisting of H and halogen. $Z^1$ is a member selected from the group consisting of —$CQ_2$—, —$CQ^1{}_2$—, —$CQ^2{}_2$—, —O—, —S—, $NR^4$—, —$C(O)NR^4$ and $R^4NC$ (O0-, in which $R^4$ is a member selected from the group consisting of H, alkyl, substituted alkyl, aryl, substituted aryl, heteroaryl and heterocyclic groups and m and n are independently a number between 0 and 40.

In yet another preferred embodiment, the organic layer comprises a compound according to Formula 5 above, in which Q, $Q^1$ and $Q^2$ are independently members selected from the group consisting of H and fluorine. In a still further preferred embodiment, the organic layer comprises compounds having a structure according to Formulae (6) and (7):

$$CF_3(CF_2)_mZ^1(CH_2)_nSH \tag{6}$$

$$CF_3(CF_2)_oZ^2(CH_2)_pSH \tag{7}$$

wherein, $Z^1$ and $Z^2$ are members independently selected from the group consisting of —$CH_2$—, —O—, —S—, $NR^4$, —$C(O)NR^4$ and $R^4NC(O)$— in which $R^4$ is a member selected from the group consisting of H, alkyl, substituted alkyl, aryl, substituted aryl, heteroaryl and heterocyclic groups. In a presently preferred embodiment, the Z groups of adjacent molecules participate in either an attractive (e.g., hydrogen bonding) or repulsive (e.g., van der Waals) interaction.

In Formula 7, m is a number between 0 and 40, n is a number between 0 and 40, o is a number between 0 and 40 and p is a number between 0 and 40.

In a further preferred embodiment, the compounds of Formulae 6 and 7 are used in conjunction with an organosulfur compound, either halogentated or unhalogenated, that bears a recognition moiety.

When the organic layer is formed from a halogenated organosulfur compound, the organic layer can comprise a single halogenated compound or more than one halogenated compound having different structures. Additionally, these layers can comprise a non-halogenated organosulfur compound.

The reactive functional groups ($X^1$ and $X^2$) are, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups which can be converted to disulfides or reacted with acyl halides;

(h) amine or sulfhydryl groups which can be, for example, acylated or alkylated;

(i) alkenes which can undergo, for example, cycloadditions, acylation, Michael addition, etc; and (j) epoxides which can react with, for example, amines and hydroxyl compounds.

The reactive moieties can also be recognition moieties. The nature of these groups is discussed in greater detail below.

The reactive functional groups can be chosen such that they do not participate in, or interfere with, the reaction controlling the attachment of the functionalized SAM component onto the substrate's surface. Alternatively, the reactive functional group can be protected from participating in the reaction by the presence of a protecting group. Those of skill in the art will understand how to protect a particular functional group from interfering with a chosen set of reaction conditions. For examples of useful protecting groups, see Greene et al., PROTECTIVE GROUPS IN ORGANIC SYNTHESIS, John Wiley & Sons, New York, 1991.

In a preferred embodiment, the SAM component bearing the recognition moiety is attached directly and essentially irreversibly via a "stable bond" to the surface of the substrate. A "stable bond", as used herein, is a bond which maintains its chemical integrity over a wide range of conditions (e.g., amide, carbamate, carbon-carbon, ether, etc.). In another preferred embodiment, the SAM component bearing the recognition moiety is attached to the substrate surface by a "cleaveable bond". A "cleaveable bond", as used herein, is a bond that is designed to undergo scission under conditions which do not degrade other bonds in the recognition moiety-analyte complex. Cleaveable bonds include, but are not limited to, disulfide, imine, carbonate and ester bonds.

In certain embodiments, it is advantageous to have the recognition moiety attached to a SAM component having a structure that is different than that of the constituents of the bulk SAM. In this embodiment, the group to which the recognition moiety is bound is referred to as a "spacer arm" or "spacer." Using such spacer arms, the properties of the SAM adjacent to the recognition moiety can be controlled. Properties that are usefully controlled include, for example, hydrophobicity, hydrophilicity, surface-activity and the distance of the recognition moiety from the plane of the substrate and/or the SAM. For example, in a SAM composed of alkanethiols, the recognition moiety can be attached to the substrate or the surface of the SAM via an amine terminated poly(ethyleneglycol). Numerous other combinations of spacer arms and SAMs are accessible to those of skill in the art.

The hydrophilicity of the substrate surface can be enhanced by reaction with polar molecules such as amine-, hydroxyl- and polyhydroxyl containing molecules. Representative examples include, but are not limited to, polylysine, polyethyleneimine, poly(ethyleneglycol) and poly(propyleneglycol). Suitable functionalization chemistries and strategies for these compounds are known in the art (See, for example, Dunn, R. L., et al., Eds. POLYMERIC DRUGS AND DRUG DELIVERY SYSTEMS, ACS Symposium Series Vol. 469, American Chemical Society, Washington, D.C. 1991).

The hydrophobicity of the substrate surface can be modulated by using a hydrophobic spacer arm such as, for example, long chain diamines, long chain thiols, $\alpha$, $\omega$-amino acids, etc. Representative hydrophobic spacers include, but are not limited to, 1,6-hexanediamine, 1,8-octanediamine, 6-aminohexanoic acid and 8-aminooctanoic acid.

The substrate surface can also be made surface-active by attaching to the substrate surface a spacer which has surfactant properties. Compounds useful for this purpose include, for example, aminated or hydroxylated detergent molecules such as, for example, 1-aminododecanoic acid.

In another embodiment, the spacer serves to distance the virus recognition moiety from the substrate or SAM. Spacers with this characteristic have several uses. For example, a recognition moiety held too closely to the substrate or SAM surface may not react with incoming analyte, or it may react unacceptably slowly. When an analyte is itself sterically demanding, the reaction leading to recognition moiety-analyte complex formation can be undesirably slowed, or not occur at all, due to the monolithic substrate hindering the approach of the two components.

In another embodiment, the physicochemical characteristics (e.g., hydrophobicity, hydrophilicity, surface activity, conformation) of the substrate surface and/or SAM are altered by attaching a monovalent moiety which is different in composition than the constituents of the bulk SAM and which does not bear a recognition moiety. As used herein, "monovalent moiety" refers to organic molecules with only one reactive functional group. This functional group attaches the molecule to the substrate. "Monovalent moieties" are to be contrasted with the bifunctional "spacer" groups described above. Such monovalent groups are used to modify the hydrophilicity, hydrophobicity, binding characteristics, etc. of the substrate surface. Examples of groups useful for this purpose include long chain alcohols, amines, fatty acids, fatty acid derivatives, poly(ethyleneglycol) monomethyl ethers, etc.

When two or more structurally distinct moieties are used as components of the SAMs, the components can be contacted with the substrate as a mixture of SAM components or, alternatively, the components can be added individually. In those embodiments in which the SAM components are added as a mixture, the mole ratio of a mixture of the components in solution results in the same ratio in the mixed SAM. Depending on the manner in which the SAM is assembled, the two components do not phase segregate into islands (See, Bain and Whitesides, *J. Am. Chem. Soc.* 111:7164 (1989)). This feature of SAMs can be used to immobilize recognition moieties or bulky modifying groups in such a manner that certain interactions, such as steric hindrance, between these molecules is minimized.

The individual components of the SAMs can also be bound to the substrate in a sequential manner. Thus, in one embodiment, a first SAM component is attached to the substrate's surface by "underlabeling" the surface functional groups with less than a stoichiometric equivalent of the first component. The first component can be a SAM component liked to a terminal reactive group or recognition group, a spacer arm or a monovalent moiety. Subsequently, the second component is contacted with the substrate. This second component can either be added in stoichiometric equivalence, stoichiometric excess or can again be used to underlabel to leave sites open for a third component.

C. Polyimides

In some embodiments, the substrates are coated with polyimide layer. It is contemplated that polyimide coated substrates are especially useful because in some instances, the surfaces homeotropically orient a liquid crystal, while in other instances the surfaces can be rubbed to provide an anisotropic surface for orient a liquid crystal. In preferred embodiments, a substrate such as a silicon wafer is coated with a polyimide. In preferred embodiment, the substrate is spin coated with the polyimide. A variety of polyimides find use with the present invention, including, but not limited to Nissan 7210, Nissan 3510, Nissan 410, Nissan 3140, Nissan 5291, and Japan Synthetic Rubber JALS 146-R19 for planar alignment of liquid crystals and Nissan 7511L and SE 1211 for homeotropic orientation of liquid crystals. Surprising, it has been found that the ability of rubbed polyimide surfaces to orient liquid crystals is maintained when a recognition moiety is displayed on the rubbed surface, and then masked when an analyte binds the recognition moiety. Thus, areas where an analyte is bound have a non-ordered liquid crystal and appear white or bright when viewed through cross polars and areas where analyte is not bound remain ordered and appear dark when viewed through cross polars. Surprising, it has also been found that polyimide surfaces that homeotropically orient liquid crystals can be used to report non-specific binding to the surface. In these embodiments, areas where an analyte is bound have a disordered liquid crystal appear white or bright when viewed through cross polars and areas where no analyte is bound maintain the homeotropic orientation and appear dark. These different polyimides provide different anchoring properties and different binding affinity to different proteins that can be used to probe and report the binding events between the proteins. Likewise, different liquid crystals show different response to the specific binding event. Therefore, it is possible to tune the assays by using different liquid crystalline materials such as, 5CB, BL093, TL 216, ZLI 5800, MLC 6613, and (p-methoxybenzylidene)-p-butylaniline (MBBA) with different optical and dielectric properties.

IV. Mesogens

Any compound or mixture of compounds which forms a mesogenic layer can be used in conjunction with the present invention. The mesogens can form thermotropic or lyotropic liquid crystals. Both the thermotropic and lyotropic liquid crystals can exist in a number of forms including nematic, chiral nematic, smectic, polar smectic, chiral smectic, frustrated phases and discotic phases.

TABLE 1

Molecular structure of mesogens suitable for use in Liquid Crystal Assay Devices

| Mesogen | Structure |
|---|---|
| Anisaldazine | $CH_3-O-\bigcirc-CH=N-N=CH-\bigcirc-O-CH_3$ |
| NCB | $C_nH_{2n+1}-\bigcirc-\bigcirc-CN$ |
| CBOOA | $C_9H_{19}-O-\bigcirc-N=CH-\bigcirc-CN$ |
| Comp A | $C_7H_{15}-\bigcirc-\bigcirc-COO-\bigcirc-NCS$ |
| Comp B | $C_8H_{17}-O-\bigcirc-O-CO-\bigcirc-O-CH_2-\bigcirc-CN$ |
| $DB_7NO_2$ | $C_7H_{15}-\bigcirc-O-CO-\bigcirc-O-CO-\bigcirc-NO_2$ |
| DOBAMBC | $C_{10}H_{21}-O-\bigcirc-CH=N-\bigcirc-CH=CH-COO-CH_2-CH\begin{smallmatrix}CH_3\\C_2H_5\end{smallmatrix}$ |

TABLE 1-continued

Molecular structure of mesogens suitable for use in Liquid Crystal Assay Devices

| Mesogen | Structure |
|---|---|
| nOm<br>n = 1, m = 4: MBBA<br>n = 2, m = 4: EBBA | 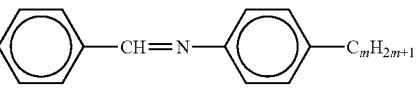 |
| nOBA<br>n = 8: OOBA<br>n = 9: NOBA | 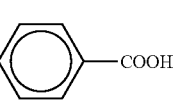 |
| nmOBC | 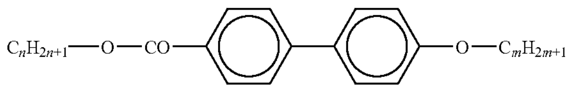 |
| nOCB | 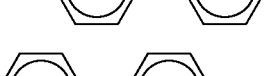 |
| nOSI | 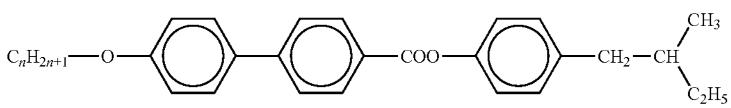 |
| 98P | 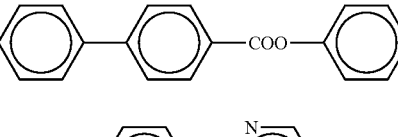 |
| PAA | 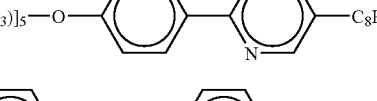 |
| PYP906 | 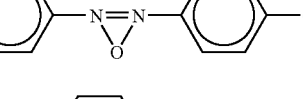 |
| n̄Sm | 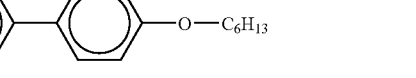 |

Presently preferred mesogens are displayed in Table 1. In a particularly preferred embodiment, the mesogen is a member selected from the group consisting of 4-cyano-4'-pentylbiphenyl, N-(4methoxybenzylidene)-4-butylaniline and combinations thereof.

The mesogenic layer can be a substantially pure compound, or it can contain other compounds which enhance or alter characteristics of the mesogen. Thus, in one preferred embodiment, the mesogenic layer further comprises a second compound, for example and alkane, which expands the temperature range over which the nematic and isotropic phases exist. Use of devices having mesogenic layers of this composition allows for detection of the analyte recognition moiety interaction over a greater temperature range.

In some preferred embodiments, the mesogenic layer further comprises a dichroic dye or fluorescent compound. Examples of dichroic dyes and fluorescent compounds useful in the present invention include, but are not limited to, azobenzene, BTBP, polyazo compounds, anthraquinone, perylene dyes, and the like. In particularly preferred embodiments, a dichroic dye of fluorescent compound is selected that complements the orientation dependence of the liquid crystal so that polarized light is not required to read the assay. In some preferred embodiments, if the absorbance of the liquid crystal is in the visible range, then changes in orientation can be observed using ambient light without crossed polars. In other preferred embodiments, the dichroic dye or fluorescent compound is used in combination with a fluorimeter and the changes in fluorescence are used to detect changes in orientation of the liquid crystal.

VI. Non-specific Detection Following Specific Capture

In some embodiments, the assays of the present find use for the non-specific detection of an analyte following specific capture. In these embodiments, the analyte is captured by a capture substrate (e.g., a PDMS stamp or bead) displaying a recognition moiety that interacts with the analyte. The analyte is then transferred to a detection substrate to which the analyte non-specifically binds. The presence of the analyte on the second (e.g., detection) substrate is detected by contacting the second substrate with a liquid crystal. Areas of disorder or order within the liquid crystal are indicative of the presence of analyte. As above, a variety of methods are useful for determining whether there are changes in the orientation of the mesogens of the device. In some embodiments, the assay devices are configured with electrodes as described above so that the analyte can be transferred to a surface of the assay device by use of an electric current (e.g., by dielectrophoresis). The electrodes are also used to measured changes in electrical properties of the device (e.g., dielectric capacitance) as a result of changes in liquid crystal orientation.

In some preferred embodiments, the assays of the present invention are used for the detection of multiple species or genera of animals to a pathogenic organism. As a non-limiting example, antibodies specific West Nile Virus have been detected in samples collected from horses, mallard ducks, pigeons, rabbits, and mice. It will be recognized that these assays find use for testing samples from avian species such as crow, blue jay, eagles, sparrows and the more than 150 species of birds present in the US that are known to be infected with West Nile Viral, horses, humans, small mammals such as dogs and cats and other companion animals, rodents such as mice and rats, etc., and other wildlife such as raccoons, skunks, felines, canids, etc.

In some embodiments, surfaces of the detection substrate as described above are functionalized for protein binding using the chemistries described above. In some preferred embodiments, the detection substrates are substrates onto which a metal (e.g., gold) has been obliquely deposited and functionalized with 4-Aminothiophenol (ATP). In preferred embodiments, it is preferred that the compound used to functionalize the surface of the detection substrate displays a stronger affinity for the ligand (e.g., an antibody) than the ligand displays for its binding partner (e.g., the envelope protein E of West Nile Virus).

In some embodiments, a stamp substrate surface is prepared that displays at least one recognition moiety. A stamp substrate is any substrate that can be used to transfer an entity that is covalently or non-covalently bound to the surface of the stamp substrate to another surface. Examples of suitable stamp substrates include, but are not limited to, PDMS and other elastomeric materials. In some embodiments, different concentrations of the same recognition moiety are arrayed in different areas of the stamp substrate. In other embodiments, a variety of different recognition moieties (e.g., envelope proteins from different enveloped viruses) are arrayed on the stamp substrate surface. In some embodiments, multiple recognition moieties in multiple concentrations are arrayed on the stamp substrate surface. In other embodiments, a control area is included on the stamp substrate surface. The recognition moiety (or recognition moieties) is then introduced to the stamp substrate surface, preferably in an array.

In some embodiments, the stamp substrate surface is a functionalized surface so that a covalent chemical bond is formed with the recognition moiety. In some preferred embodiments, a PDMS substrate is functionalized with disuccinimidyl suberate (DSS). Examples of other suitable functionalizing agents include those that are listed above. In preferred embodiments, the recognition moiety is attached via the functionalization agent.

In some embodiments, the stamp substrate is then exposed to a test sample under conditions such that an analyte (e.g., binding partner of the recognition moiety) suspected of being contained in the test sample is captured by the recognition moiety on the stamp substrate. In preferred embodiments, the test sample comprises a body fluid from a test subject. After a period incubation (e.g., 10 minutes to about 10 hours), the stamp substrate is washed. In some embodiments, the detection substrate is then contacted with the stamp substrate under conditions such that the analyte (e.g., an antibody) is transferred from the stamp substrate surface to the detection substrate. In preferred embodiments, the compound used to functionalize the surface of the detection substrate displays a stronger affinity for the analyte than does the recognition moiety so that the analyte is detached from the recognition moiety and transferred to the detection substrate.

In still further embodiments, the analyte is captured on a bead that displays a recognition moiety. As described above, the beads may be formed from latex, polymers, agarose, or other materials and in some preferred embodiments are magnetic. In some embodiments, the analyte is then transferred to the detection substrate. The transfer may be accomplished in a variety of ways. In some embodiments, the analyte is eluted from the beads either directly onto the detection substrate or eluted and the transferred to the detection substrate by a method such as spotting. In other embodiments, the beads exposed to analyte are contacted with the detection substrate so that the analyte is transferred to the detection substrate. As described above, in some embodiments, the detection substrate surface is functionalized with a moiety with a stronger affinity for the analyte than the recognition moiety on the bead so that the analyte is transferred to the detection substrate. In some embodiments, the signal from the analyte is amplified by binding one or more additional molecules to the analyte prior to elution. For example, if the analyte used is an antibody, a secondary anti-species antibody (e.g., and anti-Fc antibody for a particular species or rabbit-anti-human antibody, mouse-anti-human antibody, mouse-anti-rabbit antibody, etc.). Enzyme-antibody conjugates, analyte specific second antibodies, gold sol particles and other molecules and molecule systems may also be utilized. Where nucleic acids are being detected, the analyte detection assays outlined herein may follow an amplification method such as PCR.

A variety of detection substrates find use in the assays of the present invention, including the functionalized substrates described in detail above. In some preferred embodiments, the detection substrate comprises a rubbed polyimide or a polyimide that homeotropically orients a liquid crystal. In other embodiments, the detection substrates comprises a nanostructured gold surface (e.g., an anisotropically deposited gold surface). In some preferred embodiments, the gold surface is coated with an organic layer as described above in detail, preferably an amine-terminated organic layer such as ATP. The angle of the deposition of the gold may vary from about 5 degrees to about 80 degrees, and is preferably from about 35 degrees to about 60 degrees, and most preferably about 60 degrees. In still other embodiments, the gold surface is chemically modified with a metal carboxylate, for example, $Cr(ClO_4)_2$. In some embodiments, after transfer of the analyte to the detection substrate, a liquid crystal is applied to the detection substrate so that the presence of the binding partner on the detection substrate can be detected. A variety of liquid crystal-forming substances can be used, including those listed above. In some preferred embodiments, 5CB is used. In some embodiments, the detection substrate is used to form an optical cell with another substrate and the liquid crystal is applied to a chamber formed by the two substrates.

As can be seen, the foregoing methods can be adapted to detect of variety of analyte-recognition moiety combinations, including protein-protein, protein-nucleic acid, nucleic acid-nucleic acid, and other molecular interactions. The detection is label free. Thus, it is contemplated that this system is especially useful for multiplexed assays. As will be appreciated, the capture substrate can be functionalized with a variety of recognition moieties in an array that corresponds to a series of discreet detection regions on the detection substrate. Positive signals on the detection substrate can thus be correlated with the particular recognition moiety on the stamp substrate. Thus, a first detection area on the detection substrate can be specific for a first analyte (e.g., an antibody specific for a particular pathogen), a second detection area on the detection substrate can be specific for a second analyte (e.g., an antibody specific for a second pathogen or a different antibody specific for the first pathogen to provide confirmatory results), and so on.

In other embodiments, multiplexing is accomplished by the use of at least first and second pluralities of beads functionalized with different recognition moieties. These beads are used in conjunction with multiwell plates. In some preferred embodiments, the multiwell plate is a 8, 16, 26, 96 or 384 well plate. In some embodiments of this system, different subsets of wells in the multiwells plates (a subset can include as few as one well) contain beads functionalized with different recognition moieties. In some embodiments, solutions suspected of containing an analyte (e.g., proteins, peptides, nucleic acids, carbohydrates) are added to the wells so that the recognition moieties bind the various analytes. In some embodiments, the beads are magnetic beads and a magnet is used to attract the beads so that they can be washed with one or more wash solutions. In preferred embodiments, the magnet is positionable in relation to the wells so that the beads are attracted to the sides of the wells (see, e.g., FIGS. 18, 19 and 20). In some embodiments, the beads are treated with an elution solution so that the analyte is eluted into the solution.

The solution containing the analyte is then transferred to a substrate that orients liquid crystals as described above. A variety of methods of transfer may be used. For instance, the solution containing the analyte can be spotted onto the substrate or transferred to a microchannel in the substrate. In other embodiments, a stamp is utilized to transfer the analyte to the substrate. In these embodiments, the stamp comprising a series of projections oriented to be insertable into the well of the multiwell plate. The projections comprise a distal end that preferably comprises a material suitable for transferring the solution and thus the analyte to the substrate. In some preferred embodiments, the material is PDMS. It will be recognized that other materials described above can also be used for the stamp. In some embodiments, the substrate is prepared so that it orients a liquid crystal. In some preferred embodiments, the substrate homeotropically orients the liquid crystal. In some embodiments, the substrate is used to form a cell with a second substrate and the cell is filled with a liquid crystal. In some embodiments, the second substrate is also prepared so that is orients a liquid crystal, preferably homeotropically. In some embodiments, the presence of an analyte on the substrate is indicated by a difference in the orientation of the liquid crystal. In some preferred embodiments, the presence of the analyte is indicated by a bright field area, or randon orientation of the liquid crystal, when the liquid crystal cell is viewed through cross polar lenses. It will be appreciated that since the stamp is configured to be sued with multiwell plates, that a plate reader may be used analyze to liquid crystal cell as described above. In some particularly preferred embodiments, the beads are functionalized with antibodies or other proteins that bind cytokines. Such antibodies are known in the art and many are commercially available. The present invention is not limited the detection of any particular cytokine. Indeed, the detection of a variety of different cytokines is possible, including the following: interleukin-1 alpha, interleukin-1 beta, interleukin-2, interleukin-4, interleukin-6, interleukin-7, interleukin-8, interleukin-10, interleukin-12, GM-CSF, interferon-gamma, and TNF-alpha. In some preferred embodiments, the cytokine assay is multiplexed so that multiple cytokines can be detected in the same assay. In such a multiplexed assay, one subset of wells will contain beads functionalized with antibodies to a first cytokine, a second subset of wells will contain beads functionalized with antibodies to a second cytokine, and so on. Some of the wells may also be utilized as control wells.

In other embodiments, the present invention provides method for the selective detection of specific classes of antibodies. In these embodiments, beads are functionalized with antibodies specific for particular subclasses (e.g., IgG (e.g., IgG1, IgG2, IgG2a, IgG2b, IgG2c, IgG3, IgG4); IgM; IgA1; IgA2; IgA$_{sec}$; IgD; and IgE and combination thereof). In some embodiments, a solution suspected of containing an antibody of interest is incubated with beads functionalized with antibodies to immunoglobulins of a particular subclasses to remove those antibodies from the solution. The solution is then analyzed, preferably by a liquid crystal assay, for antibodies of the desired subclass. For example, in some embodiments, the presence of IgM, which produced during active infection, is assayed by capturing antibodies to a desired antigen with a stamp or some other means. The antibodies are transferred to a container (e.g., a well in a multiwell plate) that contains beads functionalized with anti-IgG antibodies. The solution is mixed with the beads under conditions such that the IgG is bound by the beads (i.e., removed from the solution). In some embodiments, the remaining solution is then analyzed by contacting a substrate that orients liquid crystals with the solution, forming a cell with the substrate, and filling the cell with a liquid crystal. In preferred embodiments, the substrate homeotropically orients the liquid crystal and presence of the analyte (in this case IgM immunoglobulins) is indicated by areas of disordered liquid crystal, which appear bright when viewed through cross polar lenses. In some embodiments, the transfer is performed with a stamp as described above. It will be appreciated that this system can be adapted to detect any desired subclass of immunoglobulins. For example, to detect IgA in a sample, the beads can be functionalized with anti-IgG and anti-IgM to remove IgG and IgM from the sample and so forth.

The label free detection possible with the present system provides advantages over currently used processes such as ELISA. The present system does not require a secondary antibody to detect ligand or antigen specific antibodies from a test subject. This is important because the present system can be utilized to detect antigen/ligand specific antibodies from different species in a single assay because separate secondary antibodies specific for each species are not required. This aspect greatly increases the flexibility of the assays and time needed to respond outbreaks of a disease in a wide or previously unstudied population of subjects. Furthermore, the present system does not require a labeling systems such as radioactive, fluorescent, or enzymatic system. These systems are often relatively unstable or have short shelf lives and require specialized equipment (scintillation counters, film) that is not readily adaptable to field use.

VIII. Kits

In some embodiments, the present invention provides kits for the detection of analytes. In preferred embodiments, the kits comprise one or more substrates as described in detail above. In some embodiments, the kits comprise capture and detection substrates. In some preferred embodiments, the capture substrates are beads or stamps. In further embodiments, the kits comprise a substrate that can be used in conjunction with the detection substrate to assemble a liquid crystal cell. In some embodiments, the kits comprise a vial containing mesogens. In still other embodiments, the kits comprise at least one vial containing a control analyte or analytes. In still other embodiments, the kit comprises instructions for using the reagents contained in the kit for the detection of at least one type of analyte. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

IX. Magnetic Beads in Fluidic Tubes

Current assays that utilize magnetic beads for detection of target molecules in liquid crystals include a number of steps that require handling multiple fluids at different volume scales (20-200 µl). These procedures can be laborious and time consuming. Some embodiments of the current invention are aimed at simplifying fluidic handling by integrating the fluidic part and detection part of the assays in a simple hand held device.

Figure 7:
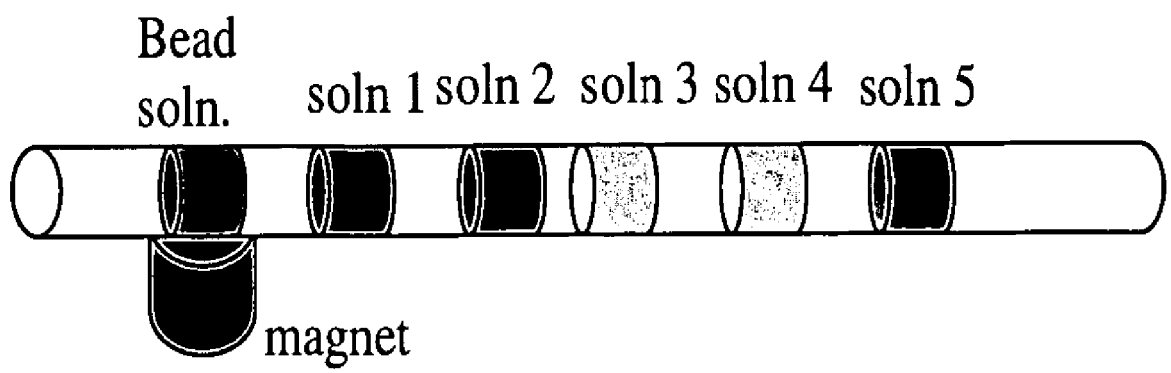
FIG. 7 presents a schematic of a magneto-fluidic assay.

When a fluid is injected in a tube (e.g. pipette) with a sufficiently small internal diameter such that the gravitational force is negligible compared to the surface tension force, stable fluid plugs separated by air pockets are generated inside the tube. If the surface tension energy is larger than the surface energy of the tube, a pressure gradient between the two ends of the tube induces movement of the fluidic plugs inside the tube without wetting the surface. Magnetic beads suspended in the fluid can be pulled down and secured at a location within the tube by applying of a magnetic field. Mixing the beads inside the tube can be achieved by generating a relative motion between the magnet and the tube. The application of a magnetic field, movement of the fluid plugs, and rotation of the tube in the magnetic field allows the magnetic beads to be mixed in the fluid. Moving the fluidic plugs through tube in or out of the magnetic field by applying a pressure or vacuum between in the tube allows for successive treatment of the magnetic beads with different reagents and capture of target from a sample. One fluid plug in the tube can be an elution buffer. The eluted buffer may be dropped on to a reporting surface that is used in conjunction with liquid crystals for detection. The principle of the operation of magneto-fluidic assay is schematically depicted in FIG. 7.

In one embodiment the current invention relates to the capture specific biological interactions such as antigen-antibody interactions, protein-protein interactions, etc. In one embodiment, the presence of sample can be reported using polyimide coated glass substrates. In other embodiments, the presence of sample can be reported using the other reporting surfaces including but not limited to rubbed polyimide, nanostructured gold surfaces, PDMS channels etc. In other embodiments, the fluidic tubes can also be integrated directly with PDMS channels so that the additional steps associated with the dropping the eluant from the tube to a reporting surface can be avoided. In one embodiment, the PDMS channels can be attached to the end of the tube and a two-way valve can direct the excess fluid to a reservoir and the eluant to the PDMS channels for reporting. The tube is not limited to a particular kind or shape. For example, interior of the tube could be in the shape of a triangle, oval, or square instead of a circle. The fluidic tube may have multiple bents or it could be made of a flexible material (e.g. rubber tubing). In other embodiments, the inner surfaces of these tubes are chemically functionalized to achieve the desired surface characteristics for forming fluidic plugs.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); l or L (liters); ml (milliliters); µl (microliters); cm (centimeters); mm (millimeters); µm (micrometers); nm (nanometers); C (degrees Centigrade); U (units), mU (milliunits); min. (minutes); sec. (seconds); % (percent); kb (kilobase); bp (base pair); PCR (polymerase chain reaction); BSA (bovine serum albumin).

Example 1

Use of Beads for Capture of an Analyte Followed by Non-specific Detection

Preparation of beads. Sera-Mag beads (0.8 µM in diameter) were functionalized with either 0.4 mg/mL EDC (Aldrich) or 1.1 mg/mL Sulfo-NHS (Pierce). First, 27 µl of 5% Sera-Mag beads were diluted in 1 mL of the functionalizing agent. Reactions were carried out 15 minutes and then quenched with 2-mercaptoethanol. The beads were washed 3 times with 25 mM MES and 37.5 mM NaCl. The washed beads were centrifuged at 11,300 rpm for 5 minutes. Removal of buffer was followed by the addition of fresh buffer. Next, 0.06 µM aF1pAb (100 µg/mL) was added for 1.5-2 hours during which the beads were rotated and mixed. The beads were quenched for amine by adding a final concentration of 10 mM D-glucosamine. The beads were then washed in PBS+ D-glucusoamine (10 mM) for 20 minutes. The beads were transferred to regular microfuge tubes blocked with BSA to prevent nonspecific binding of non-target molecules to the beads.

Detection of F1 antigen from *Yersinia pestis*. Magnetic beads were functionalized with anti-F1 polyclonal antibody as described above. A binding solution was prepared from PBS, Tween 0.05%, Heparin 50 μg/mL, and 100 mM additional NaCl. Wash solutions were prepared from PBS/Tween 0.05% and PBS/Tween 0.05%+200 mM additional NaCl. The beads were functionalized and stored in PBS at 0.135% w/v, the same concentration at which the beads were utilized. In the experiment, 1 mL of bead solution was utilized and bound up to 5 μg/mL of F1 at over 99.0%. An ELISA on F1 samples applied before and after capture on the on the beads was carried out. The F1 samples were placed on ELISA strip wells measured for levels of F1 protein using anti-F1 polyclonal antibody. The two conditions, start material and depleted material, were then graphed against absorbance 450 nm as result of ELISA colorimetric assay. This allowed to estimation of % of F1 captured by the functionalized beads. The data showed that almost all the F1 was absorbed to the beads. The F1 antigen was then eluted to a detection substrate surface comprising polyimide. The polyimide surface is prepared as follows: Undiluted polyimide 7511 liquid is applied to a slide, spin coated, pre-cured at 80° C. for 15 minutes, cured at 180° C. for one hour and stored at RT. Further, in the last step of the protocol, 10 uL 0.1M pH 2.4 glycine is mixed with the particle beads, and the tubes are then vortexed in a microfuge and placed on a magnetic stand to obtain separation of beads from supernatant. The low pH glycine serves to elute bound F1 and its antibody complex from the bead surface. 10 uL of the eluent is applied to the polyimide surface for the LC assay. Following elution, an optical cell was formed by adding a second substrate separated from the detection substrate by a thin mylar film. Mesogens (5CB) were then introduced into the optical cell.

Surfaces functionalized with polyimide 7511L orient liquid crystals in a homeotropic alignment in the absence of bound analyte. When analyte is present, the homeotropic orientation is disrupted. When viewed through cross polar lenses, homeotropic orientation is indicated by a dark field, while disrupted orientation is indicated by a bright field, as shown in FIG. 8. A digitized image taken with two Polaroid filters at cross polar configuration at 0°. Polyimide 7511L slides were prepared from 40% undiluted stock. These slides, in absence of protein, assume homeotropic alignment as shown in dark background. Upon protein binding, homeotropic alignment is disrupted and shown in white background. In the top row, from left to right, are elution samples from aF1pAb beads initially blocked with RNase A treated with BSA 400 ng/mL, F1 500 pg/mL and 2.5 ng/mL. The bottom row is 25, 100, and 400 ng/mL concentrations of F1. After initial protein binding in binding solution PBS/T/H/N, aF1pAb beads were washed in PBS/Tween 0.05%, 200 mM additional NaCl (PBS/T/N) wash solution.

An additional example demonstrates how this approach one can determine presence and quantity of the target molecule. FIG. 1 demonstrates that with increasing F1 concentration, the disruption of homeotropic alignment increases as indicated by increased white signal against aligned LC black background on homeotropic aligning polyimide surfaces. This type of assay can be used to quantify levels of the F1 antigen.

In FIG. 1, the digitized figures were taken by polarized microscope with cross polar filters (0°). Polyimide 7511L slides were prepared from 40% undiluted stock. In absence of protein, these slides assume homeotropic alignment as shown in by the dark background. Upon protein binding homeotropic alignment is disrupted (indicated by a white background). The following samples were analyzed: elution buffer, BSA (200 ng/mL), and F1 elutions of beads exposed to 5, 10, 50 and 200 ng/mL concentrations of F1. The conditions were as described above. These experiments were carried in triplicate and FIG. 1 had intermediate levels of signal with respect to two other replicates (not shown). As can be seen, it was possible to detect 5 ng/mL analyte.

FIG. 2 is a graphic representation of luminosity index for the experiment depicted in FIG. 1. These experiments were carried in triplicate and figure chosen above have intermediate levels of signal with respect to two other replicates. Elution buffer was also applied to one area and used as reference for Luminosity index shown in the graph below.

In further experiments, a rubbed polyimide surface was utilized. FIG. 3 shows a digitized image taken with a polarized microscope with cross polar filters (0 degrees). Polyimide SE 7210 1.5% slides were rubbed at 2.55 ml/m setting at 4.0 cm/s table speed with a wheel speed of 343 rpm. FIG. 3 shows the results of elutions to the polyimide surface from functionalized aF1pAb beads that were treated with various concentrations of F1 or BSA as control. After washing, the beads were treated by the addition of rabbit anti-mouse IgG (5 μg/mL) and anti-mouse FC IgG (6 μg/mL). The complex was eluted off of the beads with 10 μl acid elution of 0.1M glycine pH 2.3. Elution samples were neutralized by addition of 1 μl 1 M Tris pH 7.5. The samples were contacted with the polyimide substrate and an optical cell was constructed by placing a mylar spacer on the substrate clamping another substrate onto the first with bulldog clamp. 5CB was applied in liquid phase and after cooling the digitized image was acquired.

FIG. 4 provides the results of further experiments demonstrating the detection of an analyte (F1) from a complex medium (chicken serum). In these experiments, chicken serum (CS) was diluted to 20% with the binding solution PBS/T/H/N. BSA blocked beads functionalized as above were used. Six 0.5 mL suspensions of aF1pAb beads (0.135% concentration) were contacted with the diluted CS. After binding, all tubes were washed with PBS/Tween buffer. The beads were then washed a second time with 100 μL 0.5× PBS+2 mM SDS or 100 μL 0.1M glycine pH 4.0. After mixing, the wash buffers were removed by pelleting the beads in PBS/Tween 0.05%. The beads were then washed with PBS/Tween/NaCl (additional 200 mM). aF1mAb at 3 μg/mL was then added to the beads in 0.5 ml tubes. The reactions were mixed and the supernatant was removed. Next, 0.75 mL of 5 μg/ml of both RAM and anti-mouse FC IgG were added for 5 minutes. The beads were washed with PBS/Tween/NaCl and then with PBS. Elution buffer (10 μL) was added to each tube mixed by vortexing for 3-4 minutes. The elution buffer (2 μL aliquots) was the applied to a 7511L homeotropic polyimide slide. The slides were placed on a heated plate for 2-3 minutes until droplets have evaporated. The slides were then washed with $dH_2O$ and dried with gas nitrogen. An optical cell was constructed by using a bulldog clamp to clamp together the treated substrate and an another substrate with a mylar spacer in between. 5CB in nematic phase was applied at room temperature. After 5 minutes, the homeotropic liquid crystal was observed.

FIG. 4 is a digitized image taken with cross polar filters (0 degrees). In top row are elutions from beads treated contacted with 20% CS with no additional wash, SDS wash, and a 0.1M glycine pH 4.0 wash. In the lower row are elutions from beads contacted with 20% CS+F1 50 ng/mL with no additional wash, SDS wash, or a 0.1M glycine pH 4.0 wash. FIG. 5 presents the results of the same experiments as analyzed with a polarized microscope. The digitized images were taken by polarized microscope where the polaroid filters are cross polar at 0°. The order of the treatments is the same as for FIG. 4.

Figure 4:
FIG. 4 is an image of the results of the detection of F1 in chicken serum.
Figure 5:
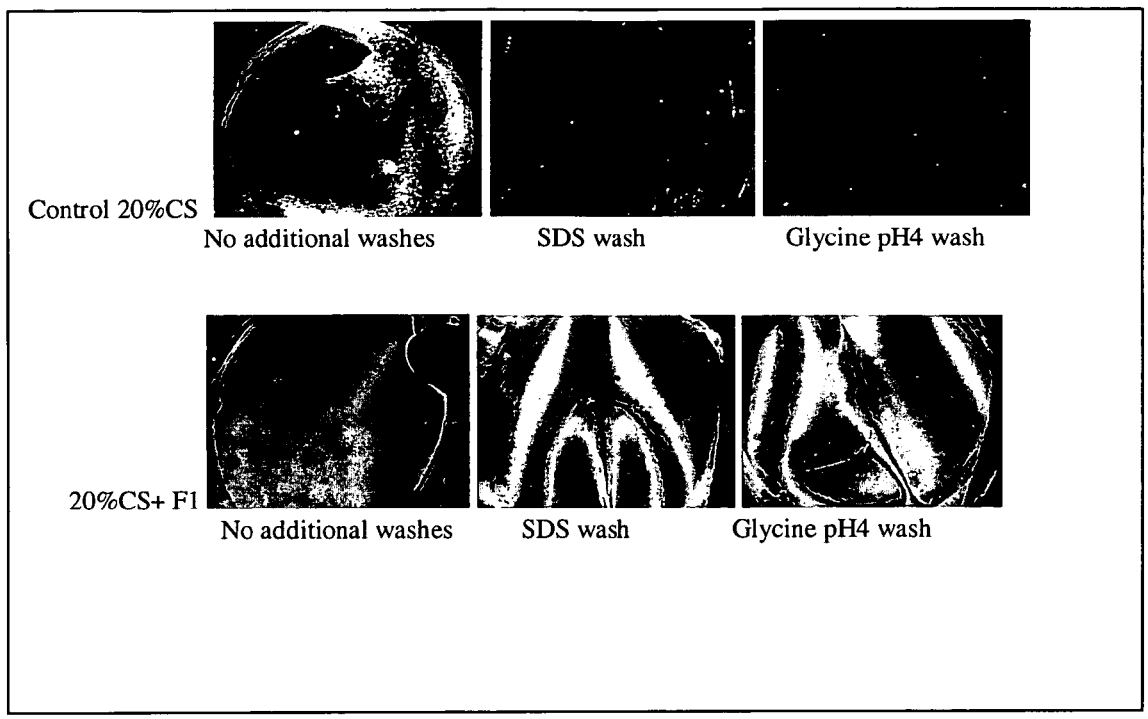
FIG. 5 is an image of the results of the same experiment as FIG. 4 taken with a polarized microscope.
Figure 6:
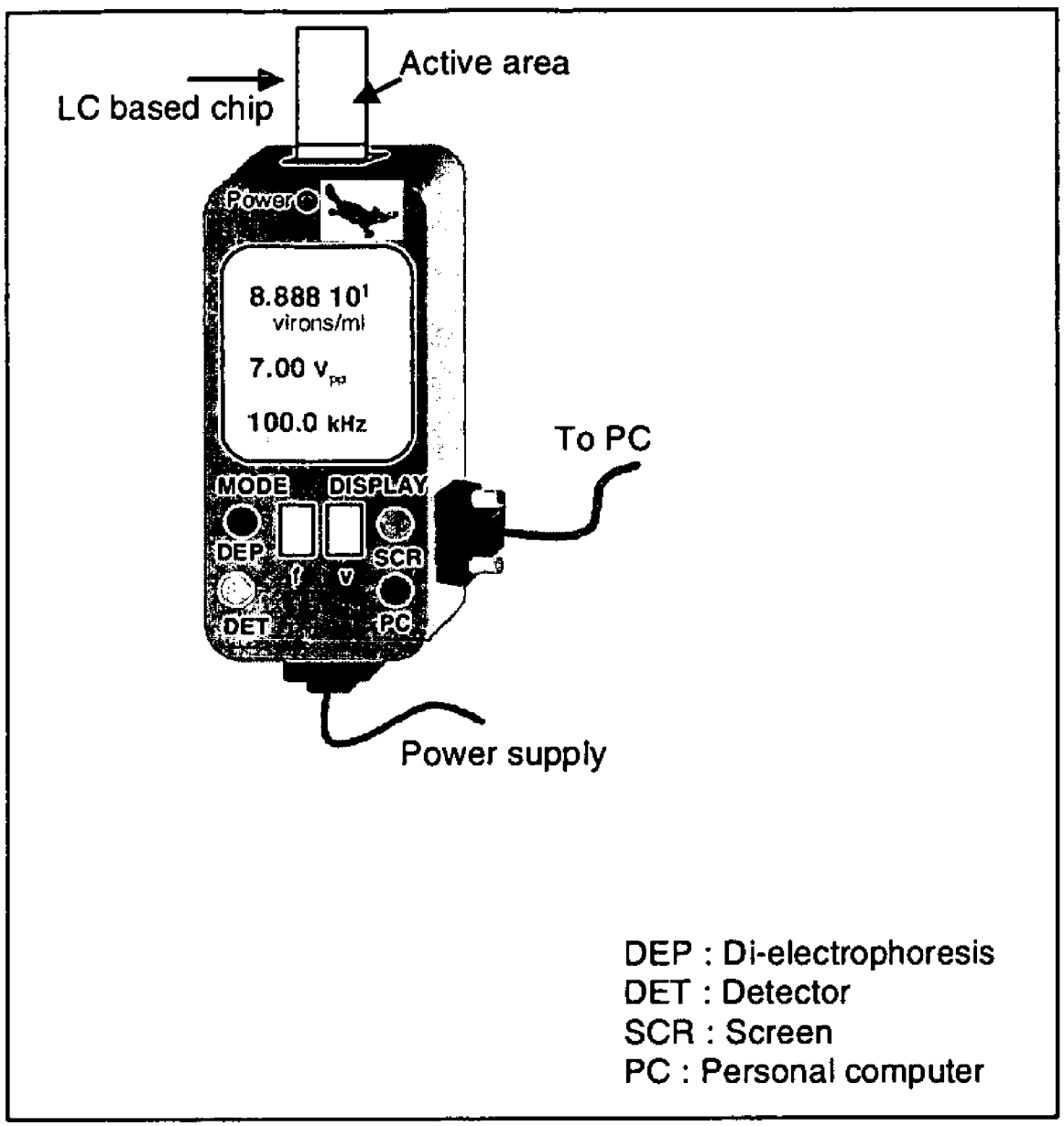
FIG. 6 is a schematic depiction of a readout device of the present invention.

The SDS and 0.1M Glycine washes were conducted to remove the BSA blocker from the functionalized beads so that there be no BSA signal interfering with F1 detection. As can be seen in FIG. 4 and FIG. 5 (polarized microscope image), both the SDS and Glycine washes eliminated the signal from the control top row second and third spots (20% Chicken Serum). Since the functionalized beads were blocked with BSA, it is most likely the BSA blocker that creates the signal seen in the first spot.

Example 2

Capturing Specific Biological Target

Magnetic beads, typically with diameter of 0.8 micron (Seradyne, Indianapolis, Ind.), are functionalized with a carboxylic acid group. Target molecules specific to a receptor (i.e., primary antibody) are immobilized onto the magnetic beads using amide chemistry. The remaining unoccupied carboxylic acid groups are then blocked with bovine serum albumin (BSA) to prevent non-specific binding. These receptor functionalized and BSA blocked magnetic beads are exposed to sample fluid containing target molecules (i.e., antigen). The magnetic beads are washed with PBS/Tween20 solution followed by SDS buffer removing nonspecifically bound proteins including the BSA. The magnetic beads are exposed to a sample containing a secondary antibody that also binds to the target molecules. A rinse with PBS/Tween20 removes the nonspecifically bound secondary antibody from the beads. The magnetic beads are subjected to an elution buffer, a low pH glycine buffer or a urea solution, that breaks the antibody-antigen binding. If the magnetic beads had any target molecules captured, the eluted sample would have both target molecules and the secondary antibody. The beads are pulled down using a magnet and the eluant is extracted. The eluted buffer is dried onto a polyimide coated surface (SE 1211 Nissan Chemicals) or passed through polydimethylsiloxane (PDMS) [Dow Chemicals] micro fluidic channels both of which align liquid crystals homeotropically (perpendicular to the surface). Finally, a liquid crystal cell is fabricated with these surfaces or liquid crystal is passed through the channels. Presence of the target molecules on the sample manifests as a random planar alignment of liquid crystals on the spots or on the micro fluidic channels which is detected by two polarizers set up in series so that their optical axes are parallel.

Example 3

Magneto-fluidic Assay

Antibody functionalized BSA blocked magnetic beads as described in Example 25 suspended in solvent are placed in a low retention tube. A magnet is positioned near the beads on the outside of the tube causing the beads to accumulate near the magnet on the inside of the tube. The solvent is removed. A binding buffer is added to the tube containing the beads. These beads are ready for capture of an antigen specific to the receptor (i.e., antibody). A 1.0 ml serological pipette (Corning Inc.) is attached to a variable flow mini pump (VWR Scientific). A plug of elution buffer (0.1 M glycine with pH 2.4) is placed within a pipette using a pressure gradient between two ends of the tube. Using air pressure the plug of elution buffer is moved through the tube allowing an air pocket to form at the end of the tube where the elusion buffer entered the tube. This is followed successively by fluid plugs containing 50-100 µl of PBS/Tween 20 (0.05%), 50-100 µl of antibody specific to the target in binding buffer (PBS/Tween 20 0.05%/NaCl 100 mM), 50-100 µl of SDS 2 mM/0.4×PBS, 50-100 µl of PBS/Tween 20 0.05% with additional 200 mM NaCl, and finally 100 µl of ~0.01% of the antibody functionalized BSA blocked magnetic beads in the binding buffer. All these fluid plugs are separated by ~100 µl air pockets. A 50 µl sample containing target molecules (i.e., antigen) in human serum is then injected to the first plug containing the magnetic beads using a syringe.

Figure 8:
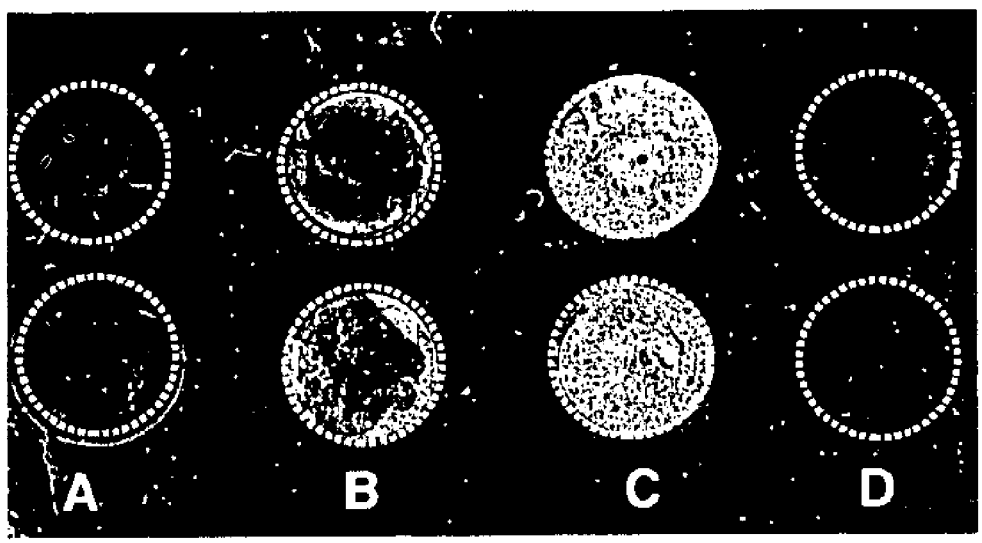
FIG. 8 is optical photographs of a liquid crystal cell between crossed polarizing films. Spots represented by dashed circles are treated with (A) elution buffer alone, (B) eluant from 50 μl of 20 ng/mL F1 from human serum, (C) eluant from 50 μL of 100 ng/mL F1 from human serum, and (D) eluant from a 50 μL of human serum without F1. The volume of the fluids spotted on each case is 10 μL. The top and the bottom rows represent the replica of the same experiment.
Figure 9:
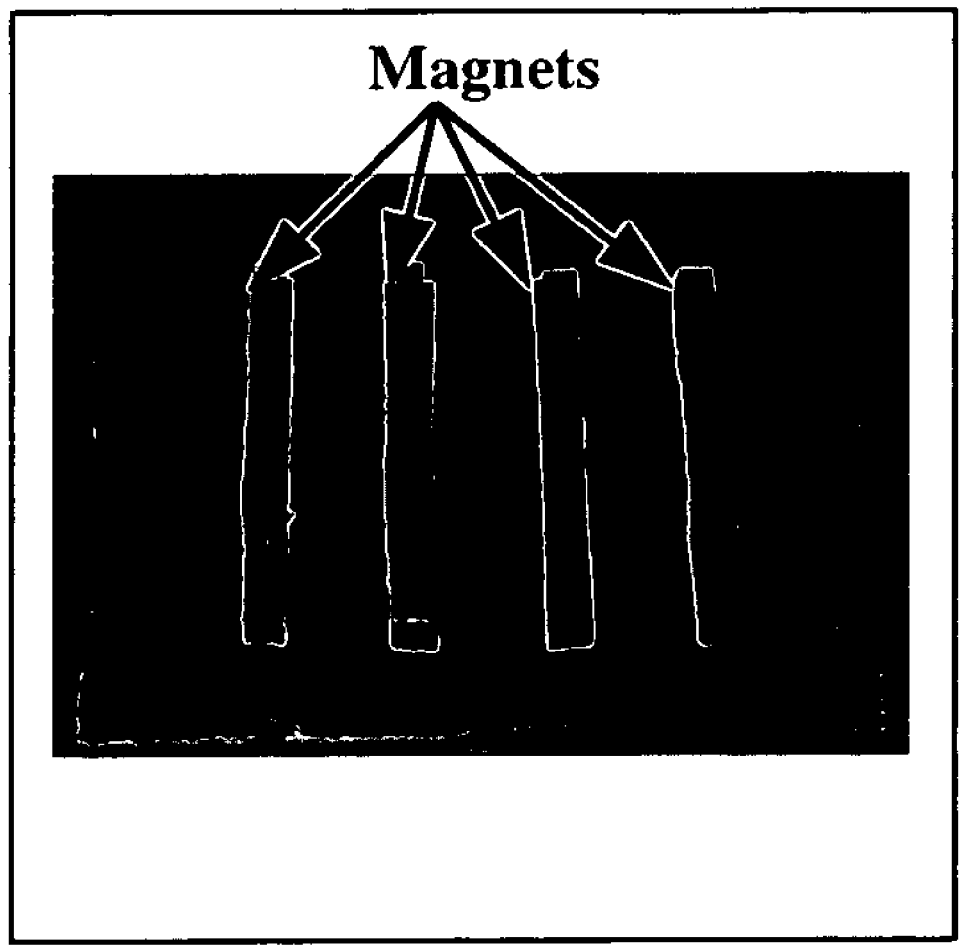
FIG. 9 is a depiction of a magnetic base place for use with a 96 well plate.
Figure 10:
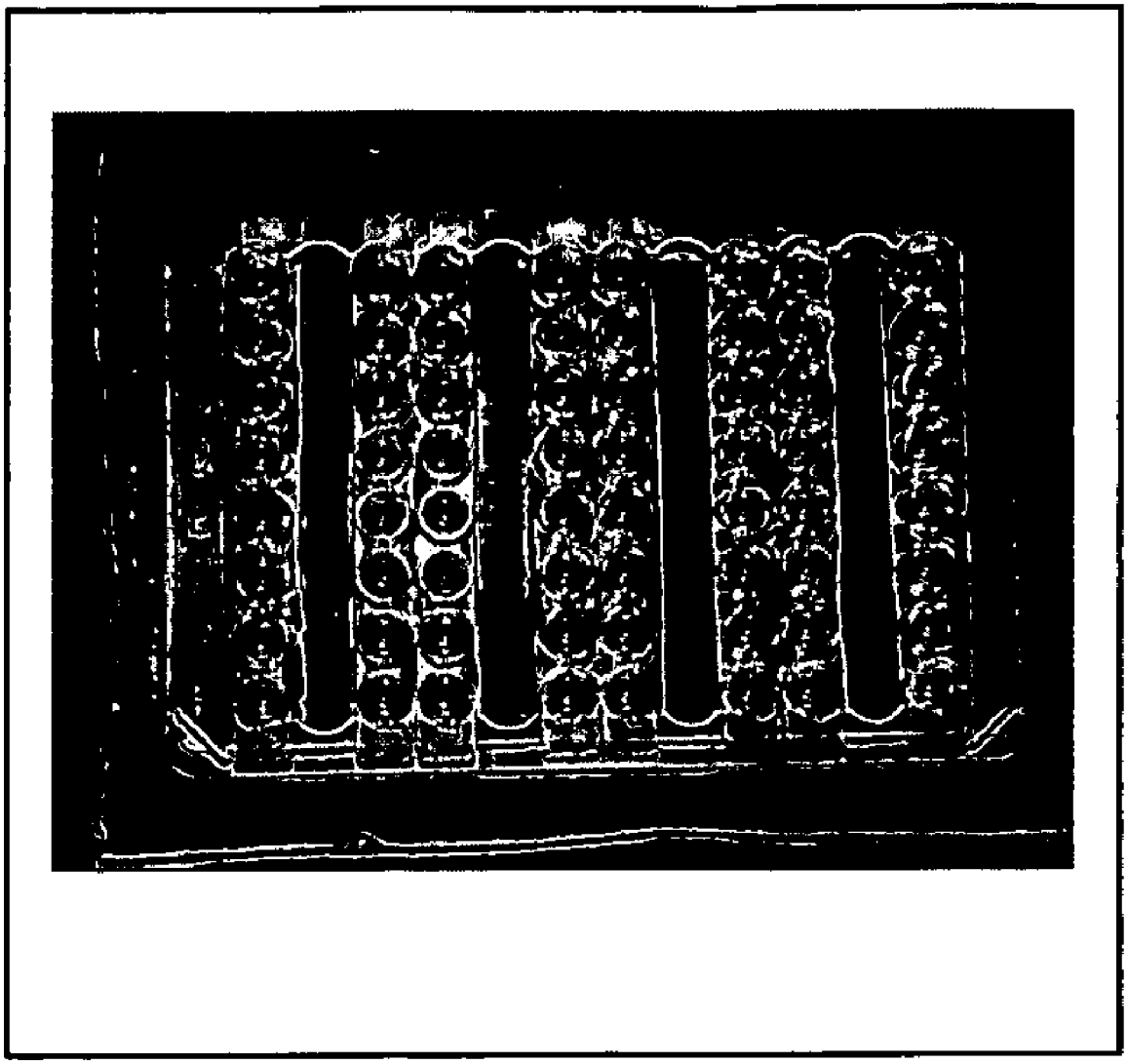
FIG. 10 is a picture of a modified 96 well plate on a magnetic base.

The pipette is mounted near a permanent magnet of strength ~2 kGauss to create a magnetized area within the pipette. The tube is slowly rotated. This introduces a rigorous mixing of the beads in the binding buffer to allow the capture of target molecules from the sample. After a few rotations of the pipette, the rotation is ceased, and the beads are pulled down at the bottom of the tube by the magnet. The binding buffer plug is then pushed across the pipette away from the magnetic beads using the pump leaving the beads bound to the bottom of the pipette in the magnetized area. The pressure gradient pushing the fluid plug through the pipette is maintained until the next fluid plug comes over to the magnetized area. Once the second fluid plug covers the beads, the pump is turned OFF and the tube is rotated again a few times to allow mixing of the beads in the fluid of the plug. Again, the beads are pulled down to the bottom of the pipette and the next fluid plug is brought over the beads in the magnetized area. This process is repeated with all the reagents in each plug until the elution buffer plug comes over to the magnetic beads. The PBS/Tween20 and the SDS buffer remove the non-specific binding whereas the secondary antibody amplifies the signal. At the end, the elution buffer comes in to contact with the beads and the pipette is rotated. This rotation causes the antibodies to come off of the beads. Finally, the beads are pulled down and the eluted buffer is dropped onto a polyimide (PI) coated glass slide. The droplet is allowed to evaporate on the surface, rinsed with water, and a liquid crystal cell is fabricated by pairing this surface with another PI coated surface separated by a 25 micron gap. The cavity is then filled with liquid crystal 5CB and the cell is observed between two crossed polarizing films (see FIG. 8).

In presence of the target in the sample, the eluant will have antibodies and target molecules in it which bind to the polyimide surface. Although the invention is not limited to any particular mechanism, we believe the presence of target molecules on the polyimide surface causes the liquid crystals to orient randomly parallel to the surface. When viewed in between crossed polarizers, the homogeneous (planar) texture oriented film of liquid crystal causes the appearance of a bright spot. On the other hand, if the sample does not contain the specific target molecules nothing comes off the beads to bind to the polyimide surface and the liquid crystals align perpendicular to the surface as dictated by the polyimide surface causing the liquid crystal to appear dark between crossed polarizers.

Figure 12:
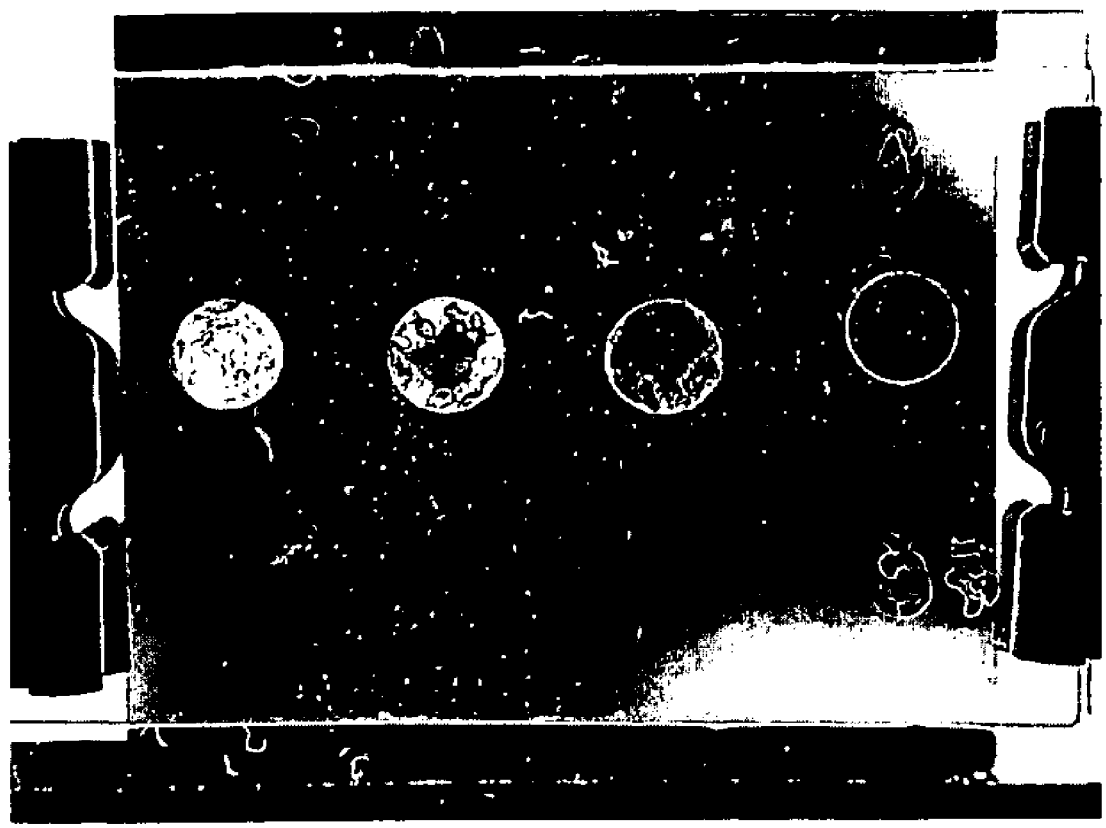
FIG. 12 is a photograph of a liquid crystal cell. The presence of the analyte (F1 antigen) is indicated by bright field (i.e., random orientation of the liquid crystal).

The lateral flow system was used to analyze the presence of F1 antigen in a sample. In the titration illustrated below, a sample as low as 1 ng/mL was readily detected, corresponding to an absolute detection limit of 50 pg of F1 antigen. Unless otherwise noted, the buffers, beads and conditions are as described in Example 22. Binding buffer 100 µL+50 µL of sample Human Sera containing 0, 1, 5, and 10 ng/mL of F1 was applied to the functionalized magnetic beads. 100 µL washes of PBS+Tween20 0.05%+200 mM NaCl and SDS 2 mM in 0.4×PBS were performed. 100 µL aF1pAb 10 µg/mL used and finally beads were washed with 100 µL PBS+ Tween20 0.05%. Finally, 20 µL sample was eluted off of the beads. All of the above steps were carried out with lateral flow liquid pockets where paramagnetic beads were mixed by moving the magnet at the location of beads. 10 uL of eluted sample was spotted on one surface of spin coated polyimide 1211 glass slide. Samples were dried, washed with dH$_2$O, and dried again with N2 stream. The bulldog clamp cell was formed using an untreated polyimide spin coated glass slide, using Mylar as spacers. 5CB liquid crystal was applied in liquid phase and after cooling the cell, a picture (FIG. 12) was taken with camera with sample place between cross polar filters at 0 degrees. Background is homeotropic alignment shown in dark vs. disruption as shown in white signal.

Example 4

Magnetofluidic Assays Using a Multiwell Format

As described above, different formats of assays that utilize magnetic beads are based on the following principle. The magnetic beads, typically with diameter of 0.8 micron (Seradyne, Indianapolis, Ind.), are functionalized with appropriate chemistries, such as with carboxyl groups. Target receptor molecules such as antibodies are then immobilized onto the beads using carbodiimide chemistry. The remaining unoccupied sites are then blocked with some other protein such as bovine serum albumin (BSA) to prevent non specific binding. These receptor functionalized and BSA blocked beads are exposed to sample fluid containing target molecules. The random, widespread distribution of the receptor functionalized beads throughout the sample fluid enhances the capture of target molecules.

These beads are washed with PBS/Tween20 solution followed by SDS buffer to remove nonspecifically bound proteins. Next, the beads are exposed to a reagent solution containing the secondary antibody capable of binding to the target molecules, and a final rinse with PBS/Tween20 removes the nonspecifically bound secondary antibody from the beads. In the absence of target molecules bound to the primary antibody there will not be any secondary antibody bound to the beads. And finally, these beads are subjected to an elution buffer (for example, a low pH glycine buffer or a urea solution) that breaks the antibody-antigen bonds. If the sample has any target molecules captured, the eluate will contain the secondary antibody and some portion of the captured target molecules. Some of the captured target molecules may stay bound to the primary antibodies on the bead surfaces and will not be eluted. Since the liquid crystal assay is designed to measure the mass of protein in a sample, the absence of a portion of a relatively low molecular weight target molecule is not considered detrimental to the overall signal generated in the assay. The bulk of the signal will result from the relatively high molecular weight secondary antibody.

The beads are pulled down using a magnet and the eluate is extracted. In order to detect presence of proteins in the eluate, the eluted sample is applied and dried down onto a polyimide coated surface (for example, SE 1211 Nissan Chemicals) or passed through polydimethylsiloxane (PDMS) [Dow Chemicals] micro fluidic channels both of which align liquid crystals homeotropically, i.e., perpendicular to the surface. Finally, a liquid crystal cell is fabricated with these surfaces or liquid crystal is passed through the channels. Presence of the target molecules on the sample manifests as a random planar alignment of liquid crystals on the spots or on the micro fluidic channels. Therefore, in the absence of eluted protein, the polyimide or PDMS surfaces display a homeotropic liquid crystal alignment yielding a dark appearance when viewed through crossed polarizing filters. In the presence of eluted protein, the surfaces display a random alignment yielding a bright appearance.

Some of the bead based formats described above involve a number of steps that include handling multiple fluids at different volume scales from 20-200 µl and fabrication of LC cells or injection to the micro fluidic channels followed by liquid crystals. These multiple steps can be both laborious and time consuming. This embodiment is aimed at simplifying these multiple fluidic handling steps and integrating the fluidic part of the assay and detection part of the assay in a simple hand held device.

The procedure described in Example 22 was conducted in individual 1.5 ml microcentrofuge tubes. This present assay has been adapted to be performed in a 96 well plate using strips of 8 wells (for example, Nunc's PlySorp® 96 well plate, Cat# 475086). The plate format allows for numerous samples to be simultaneously manipulated using a multi channel pipette.

Figure 11:
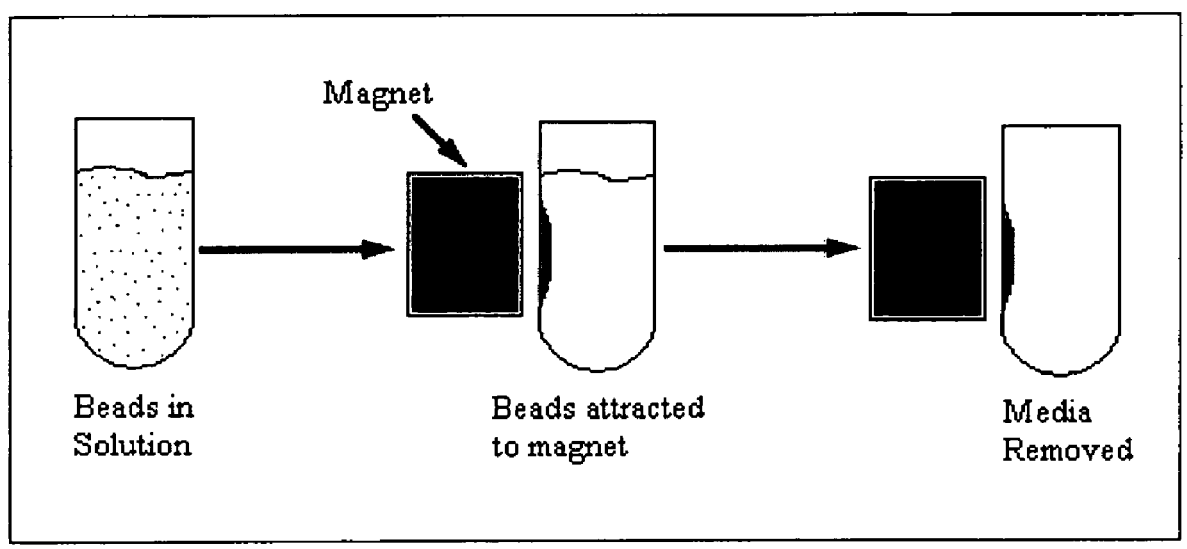
FIG. 11 is a schematic depiction of attraction of beads to the side of a well.

A base plate has been constructed consisting of a plastic base with magnets mounted at set intervals. See FIGS. 18 and 19. The 96 well plate is set onto this magnetic base plate and the beads in each well are of with magnets placed between columns of wells. The beads are attracted by the magnets to the side of the well and held in place as the media is removed for the next step. See FIG. 11. The 96 well plate is removed from the magnetic base, allowing the beads to resuspend by the addition of media from the next step of the process.

The plate format also allows for easy multiplexing, allowing for the detection of multiple agents within the same sample. The functionalized beads capture and remove only the specified antigen from the sample, leaving all non specific antigens in the sample. Once the beads are separated by the magnet, the sample is transferred to a second well. The second well contains beads functionalized against a different antigen, capturing only those specific antigens.

This procedure could be carried out several times with each well containing beads functionalized to different antigens. This would allow several tests to be run simultaneously on the same initial (50-200 µl) sample. This multiplexing ability would be extremely useful in settings that are limited by initial sample size, such as small animal veterinary medicine or pediatrics.

Example 5

Bead-based Capture of Ras on Nano or Micrometer Sized Beads for Detection

Experiments are performed first with purified Ras and purified non-specific proteins (e.g., BSA), and then validated using Ras-free cell lysates with purified Ras spiked at known concentrations. To create the Ras-free lysate, 3T3 cells are stimulated with EGF (50 nM) and then lysed (1 ml of cold lysis buffer) and centrifuged. Ras present in the extract is fully activated by addition of 5 ml of 10 mM GTPgS, and then incubated with Raf1-Ras binding domain coupled to agarose beads. After gentle mixing of the reaction mixture for 45 minutes at 4° C., the beads are separated by centrifugation. The supernatant is depleted of Ras, aliquoted, snap frozen and stored at −80° C. The absence of Ras from the extract is confirmed by using ELISA, polyacrylamide gel and Western blot analysis. Ras depleted extract is spiked with known amounts of pure Ras for quantification of Ras binding. ELISA is used to quantify the fraction of Ras captured onto beads using the following procedures. First, an ELISA standard curve is determined in order to establish the level of Ras binding to Reacti-Bind™ maleic anhydride wells (Pierce, Rockford, Ill.) using a given anti-Ras antibody concentration. Following the primary antibody, a second anti-species antibody against primary antibody is added which has a HRP conjugate. Following washes, the TMB color developing reagent is added and upon color formation, the reaction is stopped by addition of H2SO4 which also turns the color of the solution in the wells to yellow. The absorbance is read at 450 nm. Once levels of Ras in solution are correlated using the above ELISA assay, various concentrations of Ras are prepared in duplicate solutions. One solution is mixed with beads functionalized with anti-Ras antibody, the other solution is not treated with beads. After binding, the beads are separated using a magnetic stand, and the supernatant and the solution analyzed by ELISA to determine the level of Ras in solution. A number of parameters for optimization are described in greater detail below.

Choice of Antibody to Immobilize on the Magnetic Beads. A number of commercial sources of anti-Ras antibodies are available. These antibodies have been validated for use in immunoprecipitation and Western blots. These antibodies are screened for their binding activity when immobilized on the surfaces of magnetic beads. The commercial antibodies to be evaluated are: Anti-Ras, Clone RAS10; Catalog # 05-516, Upstate Biotechnology, H-Ras (C-20); Catalog # SC-520; Santa Cruz Biotechnology Inc, Pan Ras (FL-189); Catalog # SC-14022; Santa Cruz Biotechnology, Rat anti-v-H-Ras, Clone Y13-259; Catalog # 33-7200; Zymed Laboratories Inc., H-Ras (WT); Catalog # P2138; Invitrogen. Additional antibodies are evalutated as they become available. Preliminary results obtained indicate that Anti-Ras, Clone Ras 10, and rat anti-v-H Ras do possess binding activity for Ras when immobilized on micrometer sized magnetic beads.

Immobilization Chemistry. Optimal procedures to immobilize anti-Ras antibodies to the surfaces of magnetic beads presenting carboxylic acids groups and primary amine groups are identified. A number of cross-linking chemistries are evaluated. These cross-linking chemistries lead to the immobilization of antibodies in random orientations. Although, in principle, the oriented immobilization of antibodies on surfaces (e.g., via use of protein A or G, or via reaction with carbohydrates localized on the Fc region of the antibody) leads to a high binding capacity for antigen on a per antibody molecule basis, past studies have found that the areal densities of antibodies immobilized in defined orientations on surfaces are lower than the areal densities of antibodies immobilized with random orientations. Thus, current strategies for oriented immobilization of antibodies yield few benefits in terms of the preparation of surfaces with high binding capacities (antigens captured by unit area of surface). The present methods utilize immobilization of antibodies with random orientations—via primary amines on the surface of the antibodies. Chemistries and procedures leading to immobilization of antibodies without preferred orientations are substantially simpler than procedures and chemistries for oriented immobilization. A second criterion used to select the optimal immobilization chemistry is the minimization of non-specific binding of proteins to the beads. Using the ELISA-based procedures described above to determine capture of Ras, the depletion of non-specific proteins from solutions is measured to determine the extent of non-specific binding of proteins to the beads.

Two approaches to immobilization of the antibodies are evalutated. 1. For beads presenting COOH groups, NHS/EDC chemistry is used to activate the acid, and create an amide bond to primary amines on the antibodies. Following reaction with the antibodies, the surfaces of the beads are blocked with BSA. 2. For beads presenting NH2 groups, homobifunctional cross-linking chemistry is used to react the beads with primary amines on the antibodies. A number of commercial cross-linkers are available, including DSS and BS3 from Pierce (Rockford, Ill.).

Bead Size. A fundamental and general advantage of magnetic bead-based assays is the rapid mass transport of the target to a surface-immobilized binding group, by virtue of the mobility of the binding group located on a bead as opposed to a macroscopic (immobile) surface. The present invention is not limited to a particular mechanism. Nor is an understanding of the mechanism necessary to practice the present invention. Nonetheless, it is contemplated that because small beads diffuse more rapidly than large beads, that nanometer sized beads provide higher sensitivity for Ras and require shorter incubation times than larger micrometer-sized beads. Conversely, however, the small magnetic forces acting on nanometer-sized beads lead to slow rates of capture of these beads by use of external magnetic fields. Thus the optimal bead size for Ras assays that reflect these two competing factors is determined. There exist numerous commercial sources for nano- and micro-sized magnetic beads that present a variety of surface chemistries, including COOH— and NH2 chemistries for suitable for covalent attachment of anti-Ras antibodies. Nano-magnetic beads are purchased from Miltenyi Biotec (50 nm average diameter), BD Biosciences (200 nm average diameter), Stem-Cell (50 nm average diameter) and Immunicon Corporation (200 nm average diameter). In addition, micrometer-sized beads are purchased from Seradyne (0.8 µm), Ademtech (1 µm), Bioclone (1 or 5 µm), Chemagen (0.5, 1 and 5 µm), and Dynal Biotech (1 µm). These companies also sell magnets suitable for the capture of the beads. Using the antibodies and methods described above, the extent and rate of capture of Ras from solutions using these beads is asasy. The optimal bead size and chemistry that maximizes the specific capture of Ras in minimal time is determined.

Optimization of Solution Conditions. Although it is difficult to predict from a fundamental basis the influence of solution conditions (such as pH, ionic strength and temperature) on the kinetics and thermodynamics of antibody-antigen interactions, experimental measurement reveal these parameters to be important ones to control when optimizing the use of antibodies for capture of an analyte. Experiments are performed to optimize solution conditions (pH, ionic strength, temperature) for capture of Ras from buffer and cell lysates. The pH is varryed from 6.5 to 8.0. and the binding is conducted at 4° C. and 22° C. The ionic strength of the binding solution is varryed from 50-250 mM.

Additional parameters are assayed to optimize the capture of Ras on magnetic beads. For example, different chemistries are employed for immobilization (e.g., maleimide-based chemistries) of the antibodies, including the use of molecular spacers (e.g., ethylene glycol spacers) to increase the distance between the antibodies and surfaces of the beads. If non-specific adsorption of proteins on the beads is identified as a significant issue, alternative blocking strategies including grafted PEG layers on the beads and use of non-ionic surfactants (e.g., Triton surfactants) are assed.

Example 6

Transfer of Ras Captured on Magnetic Beads to Surfaces on which the Ras can be Detected The second step in conducting a Ras assay is the transfer of the Ras captured by anti-Ras-decorated magnetic beads onto nanostructured surfaces for the detection, signal amplification and reporting of Ras by using liquid crystals.

The approach to the optimization of the transfer of Ras from the beads to the capture surface is based first on the use of aqueous solutions of purified Ras, and subsequently validated using Ras-free cell lysates doped with known concentrations of Ras. A number of procedures for the transfer of Ras from beads to the reporting surfaces are assayed (see below). In some of these procedures, Ras is eluted from the beads into a solution that is subsequently spotted on the reporting surface. In these experiments, ELISA assays are used to determine the fraction of Ras captured on beads that is released into the eluant, and the fraction of Ras in the eluant that is not transferred from the eluant to the reporting surface. In other procedures described below, Ras is transferred from the beads directly to the reporting surface by physical contact of the beads with the reporting surface. This procedure has precedent in that contact printing has been shown to permit the transfer of proteins from stamps directly to reporting surfaces. In these experiments, fluorescence microscopy in combination with grey scale analysis is used to compare the relative amounts of Ras transferred to the reporting surface by the different procedures. To make use of fluorescence microscopy, the Alexa Fluor 488 label is covalently attached to Ras. To label the Ras, purified Ras protein is diluted into 2 mg/ml with 0.1M sodium bicarbonate, and then incubated with one vial of reactive Alexa Fluor 488 dye (Abs/Em: 494/519 nm) (Molecular Probes; Catalog # A 10235) for 1 hour at room temperature with stirring. The reaction mixture is applied onto a Bio-Rad BioGel P-6 size exclusion resin column pre-equilibrated with PBS and eluted with same buffer. Labeled proteins are eluted first then the unincorporated dye. The degree of labeling is determined by measuring the absorbance of the conjugated protein at 494 nm. Quantification of labeled Ras is carried using fluorescence microscopy (Axiovert 200 Zeiss fluorescence microscope) in combination with grey scale analysis of captured images. The optimal transfer process is determined by the evaluation of 4 candidate procedures:

Elution of Ras from the surface of the magnetic beads into an optimized aqueous buffer with subsequent transfer of the eluted Ras to the sensing surface. The anti-Ras antibodies are covalently attached to the beads and thus are not eluted from the beads. Once eluted into a small volume of aqueous buffer (volume to be optimized), the eluant is spotted onto the nanostructured surface, rinsed with water (to remove salts), and then imaged using fluorescence microscopy for reporting of the Ras. Parameters to be optimized in this procedure are (I) elution conditions (buffer components, pH, temperature, duration), (II) volume of eluant phase relative to bead number for each size of bead evaluated, (III) spotting conditions (volume of eluant containing Ras, adsorption time), (IV) conditions for rinsing of the reporting surface (solvent, volume, procedure). In preliminary experiments performed with the F1 antigen, elution was carried out in 0.1M aqueous glycine at pH 2.4. The beads were mixed with 20 uL of solution, for 2 minutes and the elution buffer was separated from the beads using a magnet. Preliminary experiments with F1 suggest acidic buffers are preferable for elution of antigen from antibodies, but a wide range of pHs are tested.

Direct placement of beads with captured Ras onto the nanostructured reporting surface, and in situ elution of the Ras from the beads onto the reporting surface. This procedure has the advantage of minimizing handling steps (i.e., a more integrated protocol) as compared to the first procedure described above. Following the elution of the Ras from the beads and the subsequent binding of the Ras to the nanostructured reporting surface, the magnetic beads are removed from the nanostructured surface using a magnet. Whether or not the removal of the beads is a necessary step is unknown: preliminary experiments suggest that removal of the beads may not be necessary. Experiments are conducted with the removal of beads and without bead removal from the nanostructured surface prior to adding liquid crystal to determine the need for bead removal. Finally, Ras captured on the surface is reported by using fluorescence microscopy using labeled Ras.

Use of microfluidic channels to elute Ras from beads with spatial localization of the eluted Ras onto the nanostructured detection surface. This procedure shares the attributes of the second procedure described above, but possesses the additional advantage that higher levels of spatial localization of the eluted Ras can be achieved. This leads to higher sensitivities to Ras. In this procedure, a PDMS-based microfluidic channel is placed onto the nanostructured reporting surface. Beads loaded with Ras are introduced into the microfluidic channel, and trapped in a designed entrance chamber. Trapping of the beads is facilitated by placement of a magnet at the entrance chamber. Subsequent introduction of an optimized eluant into the channel leads to the elution of the Ras from the beads and its transport by flow down the microfluidic channel where it will collect on the surfaces of the channel and be reported. Past studies have demonstrated that methyl or amine-terminated monolayers are very effective as adsorbing a wide variety of proteins from solution. Nanostructured surfaces supporting methyl- or amine-terminated monolayers are used to capture Ras in the channels. The use of the microfluidic channels enables the quantitation of the amount of Ras in a sample. The greater the amount of Ras, the longer the reaction zone within the channel. PDMS microfluidic channels with widths of ~10 um, and heights of ~2-5 μm are used. The small height of the channels ensures that Ras is rapidly collected on the nanostructured surface at the channel entrance. In these experiments, the optimized magnetic bead size and number determined as described above is used.

Direct transfer of Ras captured on magnetic beads onto nanostructured reporting surfaces. Studies have demonstrated that proteins captured on antibody-decorated PDMS stamps were transferred onto nanostructured reporting surfaces by physical contact of the stamp with the nanostructured surface. This transfer is facilitated by chemical functionalization of the nanostructured surface so as to make the interactions of the captured protein stronger with the nanostructured surface than with the stamp. This design criterion is straightforward to meet by use of surfaces presenting polar functional groups such as primary amines, carboxylic acids and metal salts. Thus, beads on which Ras is captured are contacted with the nanostructured reporting surface by mechanical means. Mechanical means to be evaluated include sonication, rocking, use of magnetic fields, and contact via use of a magnetized stamp. Using the protocols described above, beads loaded with labeled Ras are contacted with surfaces presenting amine, carboxylic acid groups and metal salts (prepared by using self-assembled monolayers on gold films), and fluorescence microscopy is used to compare the relative amounts of Ras transferred to the reporting surfaces.

Addition optimization experiments include altering the chemistry of the nanostructured surface to increase the strength of adsorption of Ras, reducing the flow rate of eluant through the channels by constricting the channel exit (this will increase the time available for adsorption of the Ras in the channel), and blocking of the channel entrance to minimize loss of Ras to the walls of the PDMS. The nanostructured surface can also be preloaded with a protein such as BSA.

Example 7

Optimization of the Design of Nanostructured Surfaces for the Reporting of Ras

This example describes the optimization of the design of nanostructured surfaces for the label-free, direct reporting of Ras using liquid crystals. Past studies have established that the orientational ordering of liquid crystals on nanostructured surfaces is influenced by the nanometer-scale topography of the surfaces as well as the chemical functionality of the surfaces. Similarly, the orientational response of liquid crystals to the presence of Ras captured on a surface is influenced by these same variables.

A range of materials are screened for their ability to report Ras via the orientational ordering of liquid crystals. Initial experiments are performed by spotting aqueous solutions of Ras of known concentrations on the surface of the nanostructured materials, rinsing the surfaces free of salts, and then placing liquid crystal into contact with the surface. Polarized light microscopy is used to image the orientational order of the liquid crystals on the nanostructured surfaces. Images are captured digitally, and analyzed using image analysis software (Image J, NIH Image). It is also possible to quantify the optical response of the liquid crystal to proteins by use of standard multiwell plate reader technology. Evaluation of the nanostructured reporting surfaces characterizes three parameters of the assay: sensitivity, dynamic range; and reproducibility. The following materials containing nanostructured surfaces are screened as candidate interfaces for the reporting of Ras:

Gold surfaces with nanometer-scale topography. Past studies have demonstrated that the physical vapor deposition of gold at oblique angles to the surface can lead to the preparation of gold films that possess a nanometer-scale topography that defines the azimuthal orientation of liquid crystals contacted with these surfaces. Proteins when bound to these surfaces mask the nanometer-scale topography, leading to an orientational ordering of the liquid crystal in the presence of the protein that is distinct from the orientational ordering of the liquid crystal in the absence of bound protein. Parameters to be optimized include (I) angle of deposition of the gold, (II) rate of deposition of the gold, (III) thickness of gold films. Past studies have demonstrated that changes in the nanometer-scale structure of these gold films, as controlled by changes in the parameters of the deposition process, can lead to dramatic changes in the orientational response of liquid crystals to captured proteins. These parameters are optimized for maximization of the sensitivity and dynamic range of detection of Ras.

Chemical functionality of nanostructured surfaces. Past studies have demonstrated that nanostructured surfaces, when decorated with self-assembled monolayers (SAMs) formed from omega-functionalized alkanethiols can orient liquid crystals in ways that depend strongly on the identity and orientation of the terminal functional group presented by the SAM. In particular, it is apparent that interactions between the terminal functional groups of the SAMs and the liquid crystals are sufficiently strong in some cases (e.g., COOH-terminated SAMs) to override the influence of the nanometer-scale topography discussed above. Past studies demonstrated that the orientational response of liquid crystals to proteins captured on such surfaces is fundamentally different from the orientational response of liquid crystals to proteins on surfaces on which the nanometer-scale topography dictates the orientation of the liquid crystal. Polycrystalline gold films deposited at oblique angles of incidence do possess an in-plane crystallographic texture that leads to the formation of SAMs with macroscopic azimuthal order (Follonier et al., 2003. Langmuir 19(25): 10501-10509, Everitt et al., 2000 Physical Review B 62: R4833-4836). The sensitivity and dynamic range of the response of liquid crystals to Ras captured on surfaces where the liquid crystal is oriented through the structure of the SAM present on the surface is evalutated. Candidate surfaces to be evaluated include HO—, HOOC—, EG, and NH2-terminated SAMs.

Titanium surfaces with nanometer-scale topography. Whereas gold films deposited at oblique angles have been widely used in past studies of the orientational behavior of liquid crystals at interfaces, it is contemplated that titanium surfaces may yield nanostructured surfaces that have robust and long-lived topographies that can orient liquid crystals. Because the melting temperature of Ti is substantially higher than gold, these films may be more robust and possess longer shelf-lives than gold films. The orientational behavior of liquid crystals on titanium surfaces prepared by oblique deposition is investigated, and the response of the liquid crystals to Ras deposited onto the surface of the Ti. Preliminary results have established the feasibility of orienting liquid crystals on Ti surfaces (which form a native oxide under standard laboratory conditions).

Polymeric surfaces with grafted aliphatic side chains. Past studies have demonstrated that surfaces presenting optimal densities of nanometer-long aliphatic chains can cause liquid crystals to adopt orientations that are perpendicular to a surface (so-called homeotropic anchoring). Optimization of the nanometer-scale architecture of these polymers has received substantial attention in the context of the design of interfaces for liquid crystal displays. This nanometer-scale interfacial architecture is used as a means to report the presence of Ras on surfaces. The approach involves the deposition of polymers (polyimides) with aliphatic side chains, and measurement of the orientational response of liquid crystals to Ras bound to these surfaces. It is contemplated that Ras bound to these surfaces prevents the homeotropic alignment of liquid crystals on these surfaces, thus leading to a readily quantifiable optical response of the liquid crystal.

In preliminary studies, polyimide SE1211 (Nissan Chemicals) was used to achieve the homeotropic alignment of liquid crystals on the surface. Although the specific structure of the polyimide is proprietary and not available, in general, these polyimides possess a number of aliphatic side chains (with n>12) attached to the main chain. When a thin (~20 nm) film of polyamic acid is cured to form polyimide film, a significant number of these aliphatic chains orient normal to the surface.

Figure 13:
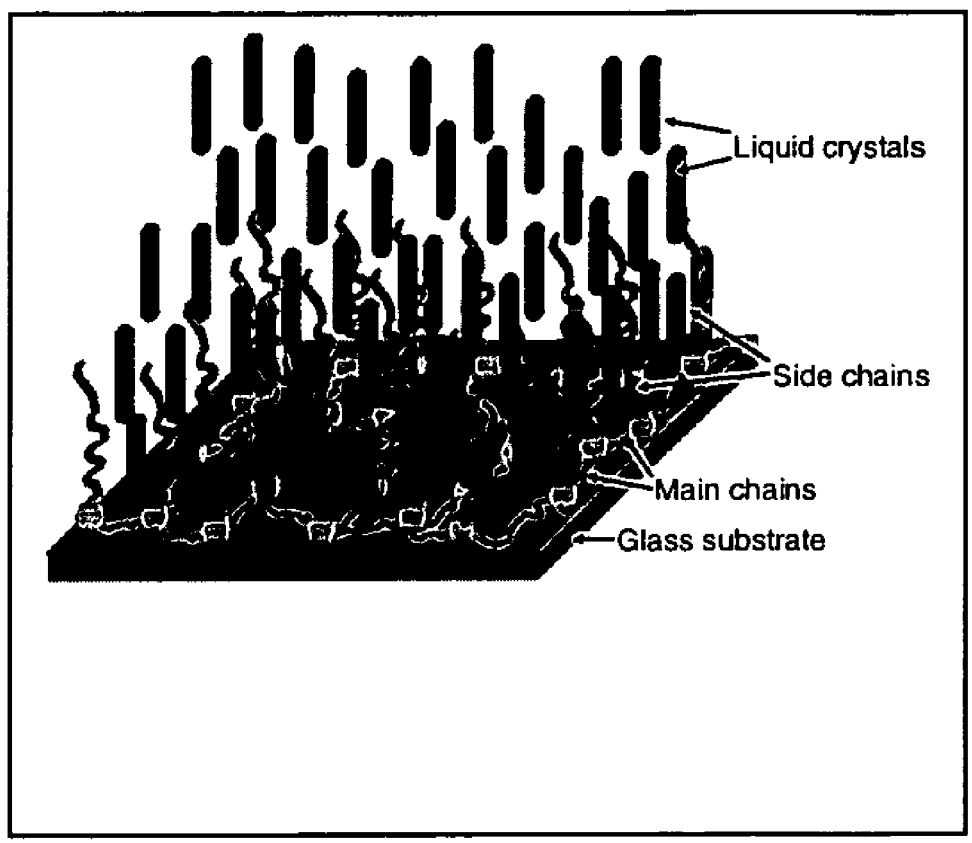
FIG. 13 shows a schematic diagram illustrating the homeotropic alignment of liquid crystals on the polyimide coated surface.

These oriented aliphatic chains provide a template for the homeotropic alignment of the liquid crystals supported on them. A schematic diagram illustrating the homeotropic alignment of liquid crystals on the polyimide coated surface is shown in FIG. 13.

Following identification of the optimal nanostructured interface for reporting of purified Ras, use of this optimal nanostructured reporting surface is combined with the results of the optimization experiments described in Examples 5 and 6 to quantitate detection of Ras from Ras-free cell lysates that are spiked with known concentrations of Ras.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in organic chemistry, materials science, chemical engineering, virology, biology, genetics, or related fields are intended to be within the scope of the following claims.

What is claimed is:

1. A system comprising:
   a) magnetic beads functionalized with a recognition moiety;
   b) a substrate that orients liquids crystals;
   c) a magnet having a magnetic field;
   d) a tube; and
   e) a pump;
   wherein said pump is fluidically connected to said tube and said tube is positioned to be exposed to said magnetic field of said magnet, said tube has an inner surface with a diameter so that the surface tension energy of a fluid plug within the tube is larger than the surface energy of the tube so that a pressure gradient between the two ends of the tube established by said pump induces movement of the fluid plugs inside the tube without wetting said inner surface, and said tube is positioned to deposit a fluid plug on said substrate that orients liquid crystals.

2. The system of claim 1, wherein said magnet is selected from the group consisting of a permanent magnet and electric magnet.

3. The system of claim 1, wherein said tube is movable with respect to said magnet.

4. The system of claim 1, wherein said tube is rotatable.

5. The system of claim 1, wherein said magnetic beads are located in said tube so as to be attractable by said magnet.

6. The system of claim 1, wherein said substrate is selected from the group consisting of a polyimide coated substrate, an anisotropic gold substrate, and a rubbed substrate.

7. The system of claim 1, wherein said substrate comprises microfluidic channels that orient liquid crystals.

8. The system of claim 1, wherein said substrate comprises polydimethylsiloxane.

9. The system of claim 1, wherein said tube is made from a material selected from the group consisting of glass and plastic.

10. The system of claim 1, further comprising a stamp.

11. The system of claim 1, further comprising mesogens.

12. The system of claim 11, wherein said mesogens are selected from the group consisting of 4-cyano-4'-pentylbiphenyl, N-(4methoxybenzylidene)-4-butlyaniline and combinations thereof.

13. The system of claim 1, wherein said recognition moiety is selected from the group consisting of a protein, peptide, polypeptide, nucleic acid, carbohydrate and organic compounds.

14. The system of claim 1, wherein said analyte is selected from the group consisting of a protein, peptide, polypeptide, nucleic acid, carbohydrate and organic compounds.

15. A method comprising:
   1) providing a sample suspected of containing an analyte, magnetic beads functionalized with a recognition moiety; a substrate that orients liquids crystals; a magnet having a magnetic field; a tube and a pump wherein said pump is fluidically connected to said tube and said tube is positioned to be exposed to said magnetic field of said magnet, said tube has an inner surface with a diameter so that the surface tension energy of a fluid plug within the tube is larger than the surface energy of the tube so that a pressure gradient between the two ends of the tube established by said pump induces movement of the fluid plugs inside the tube without wetting said inner surface, and said tube is positioned to deposit a fluid plug on said substrate that orients liquid crystals;
   2) contacting said magnetic beads with said sample by advancing a fluid plug containing said sample through said tube under conditions such that said analyte binds to said recognition moiety;
   3) attracting said beads with said magnet;
   4) washing said magnetic beads by advancing a fluid plug of washing buffer through said tube so that said magnetic beads are contacted by said washing buffer;
   5) eluting said analyte from said beads by advancing a fluid plug of elution buffer through said tube so that said magnetic beads are contacted by said elution buffer;
   6) depositing said elution buffer containing said analyte onto to said substrate; and
   7) contacting said substrate with said mesogens under conditions such that the presence of said analyte on said substrate can be detected.

* * * * *